US012593994B2

(12) United States Patent
Yuen

(10) Patent No.: US 12,593,994 B2
(45) **Date of Patent: \*Apr. 7, 2026**

(54) BLOOD PRESSURE SENSORS

(71) Applicant: Fitbit, Inc., San Francisco, CA (US)

(72) Inventor: Shelten Gee Jao Yuen, Berkeley, CA (US)

(73) Assignee: FITBIT, INC., San Francisco, CA (US)

( \* ) Notice: Subject to any disclaimer, the term of this patent is extended or adjusted under 35 U.S.C. 154(b) by 14 days.

This patent is subject to a terminal disclaimer.

(21) Appl. No.: 18/633,386

(22) Filed: Apr. 11, 2024

(65) Prior Publication Data

US 2024/0252049 A1      Aug. 1, 2024

Related U.S. Application Data

(60) Continuation of application No. 17/958,826, filed on Oct. 3, 2022, now Pat. No. 12,059,233, which is a
(Continued)

(51) Int. Cl.
*A61B 5/00* (2006.01)
*A61B 5/021* (2006.01)
(Continued)

(52) U.S. Cl.
CPC ...... *A61B 5/02116* (2013.01); *A61B 5/02125* (2013.01); *A61B 5/022* (2013.01);
(Continued)

(58) Field of Classification Search
CPC . A61B 5/02116; A61B 5/02125; A61B 5/022; A61B 5/0261; A61B 5/0295;
(Continued)

(56) References Cited

U.S. PATENT DOCUMENTS 6,331,162 B1    12/2001   Mitchell
6,583,369 B2     6/2003   Montagnino et al.
(Continued)

FOREIGN PATENT DOCUMENTS

EP           1 721 237          8/2012

OTHER PUBLICATIONS

Fuke et al., "Blood Pressure Estimation from Pulse Wave Velocity Measured on the Chest," 35th Annual International Conference of the Institute of Electrical and Electronics Engineers Engineering in Medicine and Biology Society, Osaka, Japan, Jul. 2-3, 2013, pp. 6107-6110.
(Continued)

*Primary Examiner* — Alexei Bykhovski
(74) *Attorney, Agent, or Firm* — DORITY & MANNING, P.A.

(57)          ABSTRACT

A wearable device is wearable on an appendage of a user and includes a force-sensitive display screen to generate force data when a force is applied to the force-sensitive display screen, a photoplethysmogram (PPG) sensor, and one or more processors. The PPG sensor is positioned below an external surface of the force-sensitive display screen and generates PPG sensor data when the force is applied to the force-sensitive display screen. The one or more processors are configured to: determine, from the PPG sensor data and the force data, a variation of PPG blood volume pulse amplitude with a variation in pressure applied to the appendage, and calculate an estimate of blood pressure of the appendage from the variation of PPG blood volume pulse amplitude with the variation in the pressure applied to the appendage.

20 Claims, 7 Drawing Sheets

Related U.S. Application Data division of application No. 15/452,047, filed on Mar. 7, 2017, now Pat. No. 11,457,824.

(60) Provisional application No. 62/304,909, filed on Mar. 7, 2016.

(51) Int. Cl.

| | |
|---|---|
| *A61B 5/022* | (2006.01) |
| *A61B 5/026* | (2006.01) |
| *A61B 5/0295* | (2006.01) |
| *A61B 5/11* | (2006.01) |
| *A61B 5/25* | (2021.01) |
| *A61B 8/04* | (2006.01) |
| *A61B 90/00* | (2016.01) |

(52) U.S. Cl.
CPC .......... *A61B 5/0261* (2013.01); *A61B 5/0295* (2013.01); *A61B 5/1102* (2013.01); *A61B 5/25* (2021.01); *A61B 5/681* (2013.01); *A61B 5/684* (2013.01); *A61B 5/7264* (2013.01); *A61B 5/7278* (2013.01); *A61B 5/7475* (2013.01); *A61B 8/04* (2013.01); *A61B 2090/065* (2016.02); *A61B 2560/0223* (2013.01)

(58) Field of Classification Search
CPC ......... A61B 5/1102; A61B 5/25; A61B 5/681; A61B 5/684; A61B 5/7264; A61B 5/7278; A61B 5/7475; A61B 8/04; A61B 2090/065; A61B 2560/0223; G16H 50/20
See application file for complete search history.

(56) References Cited

U.S. PATENT DOCUMENTS

| | | | |
|---|---|---|---|
| 7,479,111 | B2 | 1/2009 | Zhang et al. |
| 8,313,439 | B2 | 11/2012 | McCombie et al. |
| 10,973,422 | B2 | 4/2021 | Pantelopoulos et al. |
| 11,179,049 | B2 | 11/2021 | Niehaus et al. |
| 11,457,824 | B2 | 10/2022 | Yuen |
| 11,589,758 | B2 | 2/2023 | Pantelopoulos et al. |
| 2005/0143665 | A1 | 6/2005 | Huiku et al. |
| 2008/0043128 | A1 | 2/2008 | Poonen et al. |
| 2008/0200819 | A1 | 8/2008 | Lynn et al. |
| 2008/0262361 | A1 | 10/2008 | Gutfinger et al. |
| 2009/0105556 | A1 | 4/2009 | Fricke et al. |
| 2010/0318578 | A1 | 12/2010 | Treu et al. |
| 2010/0331145 | A1 | 12/2010 | Lakovic et al. |
| 2011/0032105 | A1 | 2/2011 | Hoffman et al. |
| 2012/0136261 | A1 | 5/2012 | Sethi et al. |
| 2012/0136605 | A1 | 5/2012 | Addison et al. |
| 2012/0274508 | A1 | 11/2012 | Brown et al. |
| 2013/0106684 | A1 | 5/2013 | Weast et al. |
| 2013/0310700 | A1 | 11/2013 | Wiard et al. |
| 2014/0012117 | A1 | 1/2014 | Mensinger et al. |
| 2014/0012147 | A1 | 1/2014 | Li et al. |
| 2014/0051941 | A1 | 2/2014 | Messerschmidt |
| 2014/0099614 | A1 | 4/2014 | Hu et al. |
| 2014/0142403 | A1 | 5/2014 | Brumback et al. |
| 2014/0155767 | A1 | 6/2014 | Fukuda et al. |
| 2014/0275854 | A1 | 9/2014 | Venkatraman et al. |
| 2014/0288435 | A1 | 9/2014 | Richards et al. |
| 2014/0358012 | A1 | 12/2014 | Richards et al. |
| 2015/0032009 | A1 | 1/2015 | LeBoeuf et al. |
| 2015/0051500 | A1 | 2/2015 | Elliott et al. |
| 2015/0112606 | A1 | 4/2015 | He et al. |
| 2015/0366469 | A1 | 12/2015 | Harris et al. |
| 2015/0374249 | A1 | 12/2015 | Elliott et al. |
| 2016/0058375 | A1 | 3/2016 | Rothkopf |
| 2016/0213331 | A1 | 7/2016 | Gil et al. |
| 2016/0261974 | A1 | 9/2016 | Arrizza |
| 2017/0024555 | A1 | 1/2017 | Flitsch et al. |
| 2017/0209053 | A1 | 7/2017 | Pantelopoulos et al. |
| 2017/0209055 | A1 | 7/2017 | Pantelopoulos et al. |
| 2017/0245769 | A1 | 8/2017 | Niehaus et al. |
| 2017/0251935 | A1 | 9/2017 | Yuen |
| 2017/0281024 | A1 | 10/2017 | Narasimhan et al. |
| 2017/0347895 | A1 | 12/2017 | Wei et al. |
| 2018/0078156 | A1 | 3/2018 | Chen et al. |
| 2018/0279965 | A1 | 10/2018 | Richard et al. |

OTHER PUBLICATIONS

Gibbs et al., "Reducing Motion Artifact in Wearable Bio-Sensors Using MEMS Accelerometers for Active Noise Cancellation", 2005 American Control Conference, Portland, Oregon, United States, Jun. 8-10, 2005, 6 pages.

Junior et al., "Estimation of Blood Pressure and Pulse Transit Time Using Your Smartphone", 2015 Euromicro Conference on Digital System Design, IEEE, 2015, pp. 173-180.

Nelson et al., "Noninvasive Measurement of Central Vascular Pressures with Arterial Tonometry: Clinical Revival of the Pulse Pressure Waveform?", Mayo Clinic Proceedings, May 2010, vol. 85, pp. 460-472.

Payne et al., "Pulse Transit Time Measured from the ECG: An Unreliable Marker of Beat-to-Beat Blood Pressure," Journal of Applied Physiology, Jan. 2006, vol. 100, pp. 136-141.

U.S. Final Office Action dated Feb. 3, 2021, in U.S. Appl. No. 15/452,047.

U.S. Final Office Action dated May 5, 2020, in U.S. Appl. No. 15/452,047.

U.S. Notice of Allowance dated Dec. 10, 2021, in U.S. Appl. No. 15/414,425.

U.S. Notice of Allowance dated Dec. 9, 2020, in U.S. Appl. No. 15/406,501.

U.S. Office Action dated Oct. 1, 2019, in U.S. Appl. No. 15/452,047.

U.S. Final Office Action dated Mar. 11, 2020, in U.S. Appl. No. 15/406,501.

U.S. Final Office Action dated Mar. 16, 2020, in U.S. Appl. No. 15/442,559.

U.S. Final Office Action dated Jul. 21, 2020, in U.S. Appl. No. 15/414,425.

U.S. Final Office Action dated Oct. 9, 2020, in U.S. Appl. No. 15/406,501.

U.S. Office Action dated Sep. 4, 2019, in U.S. Appl. No. 15/442,559.
U.S. Office Action dated Sep. 27, 2019, in U.S. Appl. No. 15/406,501.
U.S. Office Action dated Apr. 6, 2020, in U.S. Appl. No. 15/414,425.
U.S. Office Action dated May 20, 2020, in U.S. Appl. No. 15/406,501.
U.S. Office Action dated Sep. 30, 2020, in U.S. Appl. No. 15/442,559.

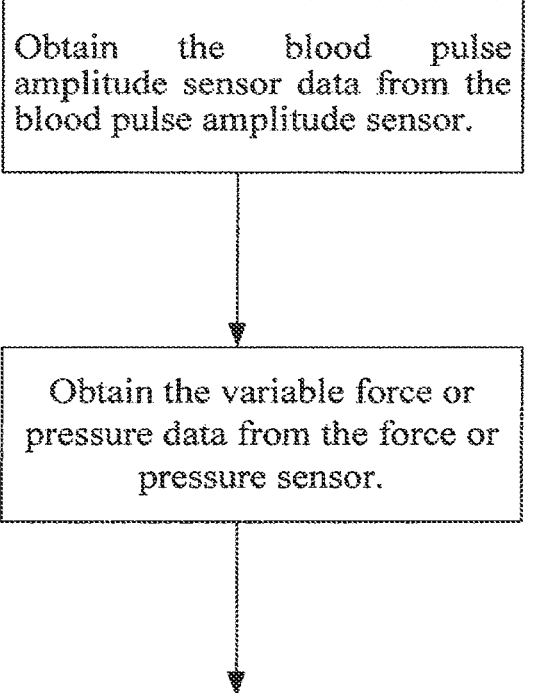

Obtain the blood pulse amplitude sensor data from the blood pulse amplitude sensor.

Obtain the variable force or pressure data from the force or pressure sensor.

Determine, from the blood pulse amplitude sensor data and the variable force or pressure data, a variation of blood pulse amplitude with a variation in pressure applied to the location where the blood pulse amplitude sensor presses against the user's body.

Determine an estimate of the user's blood pressure from the variation of blood pulse amplitude with variation in applied pressure to the location where the blood pulse amplitude sensor presses against the user's body.

Figure 2

BLOOD PRESSURE SENSORS

CROSS-REFERENCE TO RELATED APPLICATIONS

This application is a continuation of U.S. application Ser. No. 17/958,826 having a filing date of Oct. 3, 2022, which is a divisional of U.S. application Ser. No. 15/452,047 having a filing date of Mar. 7, 2017, which claims the benefit of U.S. Provisional Patent Application No. 62/304,909 filed on Mar. 7, 2016. Applicant claims priority to and the benefit of each of such applications and incorporates all such applications herein by reference in their entirety for all purposes.

BACKGROUND

A traditional blood pressure cuff works by squeezing an artery with a varying amount of pressure and "listening" for the strength of the patient's heart beating against that pressure. The pressure is exerted by an air bladder that is pumped with air. The listening is achieved with a pressure sensor that is in the air path. As the pressure goes up, the heart beat signal in the pressure sensor at first goes up and then goes back down, eventually being constricted so much that circulation is cut off. The heart beat signal from the pressure sensor is usually fit against an envelope centered at the peak of signal in order to estimate the diastolic and systolic blood pressure.

SUMMARY

One aspect of the disclosure pertains to a biometric monitoring device for estimating a user's blood pressure. The device may be characterized by the following elements: (a) a wearable fixing structure configured to attach to a user and/or a user's apparel in a manner allowing the user to wear the biometric monitoring device while performing activities; (b) a photoplethysmogram (PPG) sensor comprising a light emitter and a light detector configured to generate PPG sensor data representing blood volume pulses of variable amplitude; (c) a force or pressure sensor located and oriented with respect to the PPG sensor to generate variable force or pressure data when a user wearing the fixing structure presses the PPG sensor against a location of the user's body where the PPG sensor generates the PPG sensor data; and (d) one or more processors. In various embodiments, the one or more processors are configured to: (i) obtain the PPG sensor data from the PPG sensor, (ii) obtain the variable force or pressure data from the force or pressure sensor, (iii) determine, from the PPG sensor data and the variable force or pressure data, a variation of PPG blood volume pulse amplitude with a variation in pressure applied to the location where the PPG presses against the user's body, and (iv) determine an estimate of the user's blood pressure from the variation of PPG blood volume pulse amplitude with variation in applied pressure to the location where the PPG presses against the user's body. A related aspect of the disclosure pertains to methods that perform the operations that the one or more processors are configured to perform. Such methods may be implemented on a biometric monitoring device.

In certain embodiments, the PPG sensor is oriented with respect to the wearable fixing structure such that when the user wears the biometric monitoring device, the light emitter directs light toward a portion of the user's body on which the biometric monitoring device is worn. The location of the user's body where the PPG sensor generates the PPG sensor data may be the portion of the user's body on which the device is worn. In some designs, the portion of the user's body on which the device is worn by the user is the user's wrist. In some designs, the wearable fixing structure is a wrist band or a wrist strap, and wherein the PPG sensor and the force or pressure sensor are disposed in the wrist band or the wrist strap. In certain embodiments, the light emitter of PPG sensor is oriented to emit light into the back of the user's wrist when the user wears the biometric monitoring device. In certain embodiments, the light emitter of PPG sensor is oriented to emit light into the palm side of the user's wrist, proximate the pulse point, when the user wears the biometric monitoring device.

In some implementations, the PPG sensor is oriented with respect to the wearable fixing structure such that when the user wears the biometric monitoring device, the light emitter directs light toward a portion of the user's body on which the biometric monitoring device is not worn. More generally, the light emitter directs light away from a portion of the user's body on which the device is worn. In such embodiments, the location of the user's body where the PPG sensor generates the PPG sensor data may be the portion of the user's body on which the device is not worn. In certain embodiments, the wearable fixing structure is configured to be worn on the user's wrist, and the location of the user's body where the PPG sensor generates the PPG sensor data is a digit of the user such as the user's index finger. In some cases, the biometric monitoring device includes a capture structure configured to engage the side or the tip of the user's index finger when the PPG sensor generates the PPG sensor data from the user's index finger. In some implementations, the capture structure includes a marking of an area for the user's index finger.

In certain embodiments, the light emitter of the PPG sensor emits light outside the visible portion of the electromagnetic spectrum. For example, the light emitter may be an infrared light emitter.

In certain embodiments, the light emitter is a display screen. In such embodiments, the one or more processors may be configured to operate the display screen to depict a marking of an area for contacting the portion of the user's body on which the device is not worn. For example, the marking may be of an area for the user's finger.

In some designs, the light emitter and the force or pressure sensor are oriented such that when the light emitter emits light for generating the PPG sensor data, the light passes through the force or pressure sensor. In some designs, the PPG sensor is oriented with respect to the wearable fixing structure such that when the user presses the PPG sensor against the location of the user's body, the PPG sensor generates PPG sensor data representing blood volume pulses of a capillary bed proximate the location of the user's body. In some designs, the PPG sensor is oriented with respect to the wearable fixing structure such that when the user presses the PPG sensor against the location of the user's body, the PPG sensor generates PPG sensor data representing blood volume pulses of an artery proximate the location of the user's body.

In certain embodiments, the force or pressure sensor includes a touch sensitive display configured to generate the variable force data when a user wearing the fixing structure presses the PPG sensor against the location of the user's body where the PPG sensor generates the PPG sensor data. In some implementations, the touch sensitive display is a piezo resistive pixelated touch sensitive display. In certain embodiments, the one or more processors and/or the piezo resistive pixelated touch sensitive display is configured to determine pressure produced when the user presses the PPG sensor against the location of the user's body where the PPG sensor generates the PPG sensor data. In some embodiments, the one or more processors and/or the piezo resistive pixelated touch sensitive display is configured to determine an area occupied by pixels of the touch sensitive display detecting force caused when the user presses the PPG sensor against the location of the user's body where the PPG sensor generates the PPG sensor data. In such embodiments, the one or more processors and/or the piezo resistive pixelated touch sensitive display may be configured to determine pressure by using the force data from the touch sensitive display together with the area occupied by the pixels of the touch sensitive display detecting force caused when the user presses the PPG sensor against the location of the user's body where the PPG sensor generates the PPG sensor data.

In certain embodiments, the touch sensitive display has a pixel density that is greater in a first portion of the display screen than in a second portion of the display screen. In certain embodiments, the one or more processors and/or the touch sensitive display are configured to dynamically oversample an area of the touch sensitive display detected to be in contact with the location of the user's body where the PPG sensor generates the PPG sensor data.

In certain embodiments, the force or pressure sensor comprises a strain gauge, a button, and/or a spring. In certain embodiments, the one or more processors and/or force or pressure sensor is configured to determine pressure produced when the user presses the PPG sensor against the location of the user's body where the PPG sensor generates the PPG sensor data. In such embodiments, the one or more processors and/or force or pressure sensor may be configured to determine the pressure using (a) force detected by the force or pressure sensor, and (b) an area of a capture structure on the biometric monitoring device against which the user presses when pressing the PPG sensor against the location of the user's body.

In certain embodiments, the one or more processors are further configured to present instructions to the user to apply force to a location on the biometric monitoring device. In such cases, applying force to the location of the biometric monitoring device may press the PPG sensor against the location of the user's body where the PPG sensor generates the PPG sensor data. Further, the one or more processors may be configured to present instructions to the user to press the user's finger against the location on the biometric monitoring device. Further the one or more processors may be configured to present instructions to the user to vary the force applied to the location on the biometric monitoring device. In certain embodiments, the one or more processors are configured to present instructions to the user to vary the force applied to the location on the biometric monitoring device until the PPG sensor data shows that the user's blood volume pulses disappear or appear.

In certain embodiments, the one or more processors are further configured to present instructions to the user to adjust the position of the user's body location so that the PPG sensor is located at approximately the same elevation as the user's heart. In such embodiments, the biometric monitoring device may additionally include a motion sensor, and the one or more processors may be further configured to use data generated by the motion sensor to determine whether the PPG sensor is located at approximately the elevation as the user's heart. In some designs the motion sensor is selected from the group consisting of an accelerometer, an altimeter, a global positioning systems (GPS) detector, and a gyroscope. In some designs, the one or more processors are further configured to provide feedback when it is determined that the PPG sensor is located at approximately the elevation of the user's heart.

In some implementations, the biometric monitoring device additionally includes a display screen, and the one or more processors are further configured to present the instructions to the user via the display screen.

In certain embodiments, the one or more processors are further configured to order the amplitudes of the blood volume pulses from the PPG data so that the amplitudes vary with pressure caused by the user pressing the PPG sensor against the location of the user's body where the PPG sensor generates the PPG sensor data.

In certain embodiments, the one or more processors are further configured to: (v) obtain pulse transit time (PTT) data for the user; and (vi) calibrate the PTT data using the user's blood pressure determined from the variation of PPG blood volume pulse amplitude with variation in applied pressure to the location where the PPG presses against the user's body. In such embodiments, the one or more processors may be configured to: obtain the PTT data at first rate; and determine the user's blood pressure from the variation of PPG blood volume pulse amplitude with variation in applied pressure at a second rate, with the first rate being greater than the second rate. In some designs, the biometric monitoring device additionally includes an EKG electrode configured to be placed on a portion of the user's body where the EKG electrode generates EKG electrode data for determining PTT. As an example, the one or more processors may be further configured to generate the PTT data by using the EKG electrode data and the PPG sensor data.

In some embodiments, the one or more processors are configured to obtain the PTT data from the PPG sensor data and data from another sensor. For example, the other sensor may be an EKG electrode, a phonocardiography (PCG) sensor, ballistocardiography (BCG) sensor, an impedance plethysmography (IPG) sensor, a ultrasound sensor, or a force sensor.

In certain embodiments, the biometric monitoring device additionally includes a wireless transmitter configured to transmit the PPG sensor data and the variable force or pressure data to a remote device, and wherein the one or more processors are located in the remote device. In certain embodiments, the PPG sensor, the force or pressure sensor, and the one or more processors are integrated in the wearable fixing structure. In certain embodiments, the force or pressure sensor and the PPG sensor are within and/or directly attached to an enclosure that is part of or affixed to the wearable fixing structure.

In some implementations, the biometric monitoring device additionally includes a protrusion from the wearable fixing structure, where the PPG sensor and the force or pressure sensor are disposed within the protrusion. In some implementations, the wearable fixing device and the PPG are configured to position the PPG sensor against the pulse point on the palm side of the user's wrist when the biometric monitoring device is worn by the user.

Another aspect of the disclosure pertains to methods for estimating a user's blood pressure implemented on a biometric monitoring device. Such biometric monitoring device may include: (a) a photoplethysmogram (PPG) sensor comprising a light emitter and a light detector configured to generate PPG sensor data representing blood volume pulses of variable amplitude, (b) a force or pressure sensor located and oriented with respect to the PPG sensor to generate variable force or pressure data when a user wearing the biometric monitoring device presses the PPG sensor against a location of the user's body where the PPG sensor generates the PPG sensor data, and (c) one or more processors. The methods may be characterized by the following operations: (i) obtaining the PPG sensor data from the PPG sensor, (ii) obtaining the variable force or pressure data from the force or pressure sensor, (iii) determining, by the one or more processors and from the PPG sensor data and the variable force or pressure data, a variation of PPG blood volume pulse amplitude with a variation in pressure applied to the location where the PPG presses against the user's body, and (iv) determining, by the one or more processors, an estimate of the user's blood pressure from the variation of PPG blood volume pulse amplitude with variation in applied pressure to the location where the PPG presses against the user's body.

In certain embodiments, the PPG sensor is oriented with respect to a wearable fixing structure such that when the user wears the biometric monitoring device, the light emitter directs light toward a portion of the user's body on which the biometric monitoring device is worn. In such cases, the location of the user's body where the PPG sensor generates the PPG sensor data is the portion of the user's body on which the device is worn. In certain embodiments, the portion of the user's body on which the device is worn by the user is the user's wrist. In certain embodiments, the wearable fixing structure includes a wrist band or a wrist strap, and the PPG sensor and the force or pressure sensor are disposed in the wrist band or the wrist strap. In certain embodiments, the light emitter of PPG sensor is oriented to emit light into the back of the user's wrist when the user wears the biometric monitoring device.

In certain embodiments, the PPG sensor is oriented with respect to a wearable fixing structure such that when the user wears the biometric monitoring device, the light emitter directs light toward a portion of the user's body on which the biometric monitoring device is not worn. For example, the light may be directed away from the portion of the user's body. In some cases, the location of the user's body where the PPG sensor generates the PPG sensor data is the portion of the user's body on which the device is not worn. In certain implementations, such wearable fixing structure is configured to be worn on the user's wrist, and the location of the user's body where the PPG sensor generates the PPG sensor data is a digit of the user. In some cases, the digit is the user's index finger, and obtaining the PPG sensor data includes obtaining PPG sensor data from the user's index finger. In some implementations, the biometric monitoring device further includes a capture structure configured to engage the side or tip of the user's index finger when the PPG sensor generates the PPG sensor data from the user's index finger.

In some implementations, the light emitter is a display screen. In some such implementations, the methods additionally include operating the display screen to depict a marking of an area for contacting the portion of the user's body on which the device is not worn. For example, the marking may be an area for the user's finger.

In certain embodiments, the light emitter and the force or pressure sensor are oriented such that when the light emitter emits light for generating the PPG sensor data, the light passes through the force or pressure sensor. In certain embodiments, the PPG sensor is oriented with respect to the wearable fixing structure such that when the user presses the PPG sensor against the location of the user's body, the PPG sensor generates PPG sensor data representing blood volume pulses of a capillary bed proximate the location of the user's body. In certain embodiments, the PPG sensor is oriented with respect to the wearable fixing structure such that when the user presses the PPG sensor against the location of the user's body, the PPG sensor generates PPG sensor data representing blood volume pulses of an artery proximate the location of the user's body.

In certain embodiments, the biometric monitoring device additionally includes a display screen, and the methods additionally include presenting the instructions to the user via the display screen.

In certain embodiments, the force or pressure sensor includes a strain gauge, a button, and/or a spring. In certain embodiments, the force or pressure sensor includes a touch sensitive display, which generates the variable force data when a user wearing the fixing structure presses the PPG sensor against the location of the user's body where the PPG sensor generates the PPG sensor data. For example, the touch sensitive display is a piezo resistive pixelated touch sensitive display. In certain embodiments, the method additionally includes determining a pressure produced when the user presses the PPG sensor against the location of the user's body where the PPG sensor generates the PPG sensor data. As an example, the method may include (i) determining an area occupied by pixels of the touch sensitive display detecting force caused when the user presses the PPG sensor against the location of the user's body where the PPG sensor generates the PPG sensor data, and (ii) determining pressure by using the force data from the touch sensitive display together with the area occupied by the pixels of the touch sensitive display detecting force caused when the user presses the PPG sensor against the location of the user's body where the PPG sensor generates the PPG sensor data.

In embodiments including a touch sensitive display, the display may have a pixel density that is greater in a first portion of the display screen than in a second portion of the display screen. In certain embodiments, the methods additionally include dynamically oversampling an area of the touch sensitive display detected to be in contact with the location of the user's body where the PPG sensor generates the PPG sensor data. In certain embodiments, the methods additionally include an operation of determining the variable pressure data using: (i) force detected by the force or pressure sensor, and (ii) an area of a capture structure on the biometric monitoring device against which the user presses when pressing the PPG sensor against the location of the user's body.

In certain embodiments, the methods additionally include an operation of presenting instructions to the user to apply force to a location on the biometric monitoring device, and the act of applying force to such location of the biometric monitoring device presses the PPG sensor against the location of the user's body where the PPG sensor generates the PPG sensor data. Some such embodiments may additionally include an operation of presenting instructions to the user to press the user's finger against the location on the biometric monitoring device. Alternatively or additionally, embodiments may additionally include an operation of presenting instructions to the user to vary the force applied to the location on the biometric monitoring device. Such embodiments, may additionally include presenting instructions to the user to vary the force applied to the location on the biometric monitoring device until the PPG sensor data shows that the user's blood volume pulses disappear or appear.

In certain embodiments, the methods additionally include an operation of presenting instructions to the user to adjust the position of the user's body location so that the PPG sensor is located at approximately the same elevation as the user's heart. In such embodiments, the biometric monitoring device may additionally include a motion sensor, in which case the methods may use data generated by the motion sensor to determine whether the PPG sensor is located at approximately the elevation as the user's heart. In certain embodiments, the methods additionally include an operation of providing feedback when it is determined that the PPG sensor is located at approximately the elevation of the user's heart.

In certain embodiments, the methods additionally include an operation of ordering the amplitudes of the blood volume pulses from the PPG data so that the amplitudes vary with pressure caused by the user pressing the PPG sensor against the location of the user's body where the PPG sensor generates the PPG sensor data.

In some implementations, the methods additionally include the following operations: (v) obtaining pulse transit time (PTT) data for the user; and (vi) calibrating the PTT data using the user's blood pressure determined from the variation of PPG blood volume pulse amplitude with variation in applied pressure to the location where the PPG presses against the user's body.

In some such implementations, the methods include the following operations: obtaining the PTT data at first rate; and determining the user's blood pressure from the variation of PPG blood volume pulse amplitude with variation in applied pressure at a second rate. In some cases, the first rate is greater than the second rate.

In some such implementations, the biometric monitoring device additionally includes an EKG electrode configured to be placed on a portion of the user's body where the EKG electrode generates EKG electrode data for determining PTT. In some such implementations, the methods additionally include obtaining the PTT data from the PPG sensor data and data from another sensor. As an example, the other sensor is an EKG electrode, a phonocardiography (PCG) sensor, ballistocardiography (BCG) sensor, an impedance plethysmography (IPG) sensor, a ultrasound sensor, or a force sensor. In some such implementations, the methods generate the PTT data by using EKG electrode data and the PPG sensor data.

In certain embodiments, the biometric monitoring device additionally includes a wireless transmitter, and the methods additionally include transmitting the PPG sensor data and the variable force and/or pressure data to a remote device.

Another aspect of the disclosure pertains to methods of estimating a user's blood pressure, which methods may be characterized by the following operations: (a) presenting instructions to a user on a wrist-worn device, wherein the instructions instruct the user to apply a variable force to a location on the users body where the user is wearing a biometric monitoring device comprising a PPG sensor and a force or pressure sensor; (b) measuring a force or pressure variation data from the force or pressure sensor, wherein the measured force or pressure variation data results from the user applying a variable force to underlying blood vessel or vessels at the location on the users body; (c) detecting blood volume pulses responsive to heartbeats of the user in one or more blood vessels underlying the location on the user's body, wherein variations in the amplitude of the blood volume pulses are responsive to the user's application of variable force to the location on the user's body; and (d) determining an estimate of the user's blood pressure from a detected variation of the amplitude of the blood volume pulses with respect to a variation in pressure on the underlying blood vessel or vessels resulting from the applied variable force.

Another aspect of the disclosure pertains to a wrist-worn device that may be characterized by the following features: a piezo resistive force-sensitive display screen; a PPG sensor adjacent to or embedded in the force-sensitive screen; and control logic configured to: (i) generate one or more sensor data samples, each sensor data sample including data that links force data generated when a user presses a finger against the force-sensitive screen at a given time with heart rate data obtained from the PPG sensor at the given time; and (ii) calculate an estimate of blood pressure from the one or more sensor data samples.

In certain embodiments, the control logic is further configured to: use the force data and an area of the user's finger contacting the display screen to derive pressure applied by the user pressing the finger against the force-sensitive screen. In certain embodiments, the control logic is further configured to cause the force-sensitive screen to emit light pulses that are detected by the PPG sensor to generate the heart rate data. In certain embodiments, the force-sensitive display screen has a greater density of pixels in the center of the display screen than in the periphery of the display screen.

Another aspect of the disclosure pertains to a wrist-worn device that may be characterized by the following features: an external surface that is not in contact with the user when the wrist-worn device is worn; a force sensor; a PPG sensor disposed on the backside of the wrist-worn device; and control logic configured to: (i) generate one or more sensor data samples, each sensor data sample including data that links force data generated by the force sensor when a user presses a finger against the external surface at a given time with heart rate data obtained from the PPG sensor at the given time; and (ii) calculate an estimate of blood pressure from the one or more sensor data samples. As examples, the force sensor may be a force sensitive touch screen or film, a strain gauge integrating into the device, or a calibrated spring element configured to be pressed by the user. In certain embodiments, the force sensor is a force sensitive display screen, and the control logic is configured to cause the force-sensitive display screen to emit light pulses that are detected by the PPG sensor to generate the heart rate data.

In certain embodiments, the force sensor is configured to measure actuation by the user. In certain embodiments, the force sensor is integrated into a top surface of the wrist-worn device. In certain embodiments, the force sensor and the PPG sensor are integrated into a back side of the wrist-worn device, and the back side includes the external surface. In certain embodiments, the force sensor and the PPG sensor are integrated into a palm side of the wrist-worn device.

Another aspect of the disclosure pertains to a biometric monitoring device for estimating a user's blood pressure, which device may be characterized by the following elements: (a) a wearable fixing structure configured to attach to a user and/or a user's apparel in a manner allowing the user to wear the biometric monitoring device while performing activities; (b) a PPG sensor comprising a light emitter and a light detector configured to generate PPG sensor data representing blood volume pulses of variable amplitude; (c) a force or pressure sensor proximate the PPG sensor and oriented to generate variable force or pressure data when a user wearing the fixing structure presses the PPG sensor against a location of the user's body where the PPG sensor generates the PPG sensor data; and (d) one or more processors configured to: (i) obtain the PPG sensor data from the PPG sensor, (ii) obtain the variable force or pressure data from the force or pressure sensor, (iii) determine, from the PPG sensor data and the variable force or pressure data, a pressure value, of pressure applied to the location where the PPG sensor presses against the user's body, at which the PPG blood volume pulse amplitude falls below a amplitude threshold, and (iv) determine an estimate of the user's systolic blood pressure from the pressure value. In some implementations, the amplitude threshold is substantially 0 amplitude.

Another aspect of the disclosure concerns methods of estimating a user's blood pressure, where such methods may be characterized by the following operations: (a) presenting instructions to a user on a wrist-worn device, wherein the instructions instruct the user to vary a force applied to a location on the users body where the user is wearing a biometric monitoring device comprising a PPG sensor and a force or pressure sensor; (b) measuring a force or pressure variation data from the force or pressure sensor, where the measured force or pressure variation data results from the user applying a variable force to underlying blood vessel or vessels at the location on the users body; (c) detecting blood volume pulses responsive to heartbeats of the user in one or more blood vessels underlying the location on the user's body, where variations in the amplitude of the blood volume pulses are responsive to the user's application of variable force to the location on the user's body; (d) determining a pressure value, of pressure applied to the location where the PPG sensor presses against the user's body, at which the PPG blood volume pulse amplitude falls below an amplitude threshold; and (e) determining an estimate of the user's systolic blood pressure from the pressure value. In certain implementations, the amplitude threshold is substantially 0 amplitude.

These and other features of the disclosure are described in further detail below with reference to the associated drawings.

BRIEF DESCRIPTION OF THE DRAWINGS

FIG. 2 provides a flow chart depicting a sequence of operations for determining an estimate of a user's blood pressure from blood pulse amplitude data and force or pressure data.

DETAILED DESCRIPTION

Introductory Example

In contrast to a traditional blood pressure cuff, blood pressure may instead by measured by actuating an artery against a pressure sensor. For instance, by pushing the side of the index finger (where the radial artery resides) against a force sensor whilst a photoplethysmogram or other blood flow pulse sensor measures the volume of blood passing through the artery. The user may be instructed on how much force to apply with his finger by providing visual or audio feedback with the readings from the force sensor. In this manner, signals corresponding to those of traditional blood pressure cuff are captured: a varying and known force/pressure against an artery and a measure of the heart beat signal (via e.g., PPG) to that force/pressure. Notably, a force is what may be measured but a pressure is what is important to know. The shape of the force sensor may be shaped in such a way as to accept the finger so that the relationship of force to pressure is well understood (e.g., linear).

Sensed Signals Used for Estimating Blood Pressure

Systolic and or diastolic blood pressure readings can be obtained by measuring variations in the amplitude of pulses in blood vessels such as pulses in the volume of blood through arteries or capillary beds. Systolic blood pressure can be obtained by determining the applied pressure value at which blood flow is occluded in underlying blood vessels. The pulses are caused by an organism's heartbeats.

Variations in blood pulse amplitude can be induced by applying varying external pressure against the blood vessels. In conventional oscillometric techniques for measuring blood pressure, an inflatable cuff applies the varying external pressure. In various embodiments of this disclosure, a user manually pushes against a location on his or her body and thereby applies the varying external pressure on the underlying blood vessels. And while the user manually applies variable pressure, a sensor measures the blood pulse amplitude. A measuring device estimates the user's blood pressure from the pulse amplitude as a function of externally applied pressure.

In various embodiments, the blood pulse amplitude is determined using an optical sensor such as a PPG sensor, which measures variations in blood volume through arteries. By measuring variations in amplitude of the PPG signal (and hence variations in blood volume amplitude pulses), as a function of variations in external pressure applied to the blood vessels used to generate PPG signal, sufficient information can be acquired to determine the systolic and/or diastolic blood pressure of a user.

In accordance with various embodiments, a user applies a variable pressure to his or her blood vessels while a PPG sensor measures the amplitude of blood volume pulses. The resulting PPG signal and associated pressure data is used to calculate blood pressure. Standard approaches to determining blood pressure from oscillometric data can be used.

Figure 1:
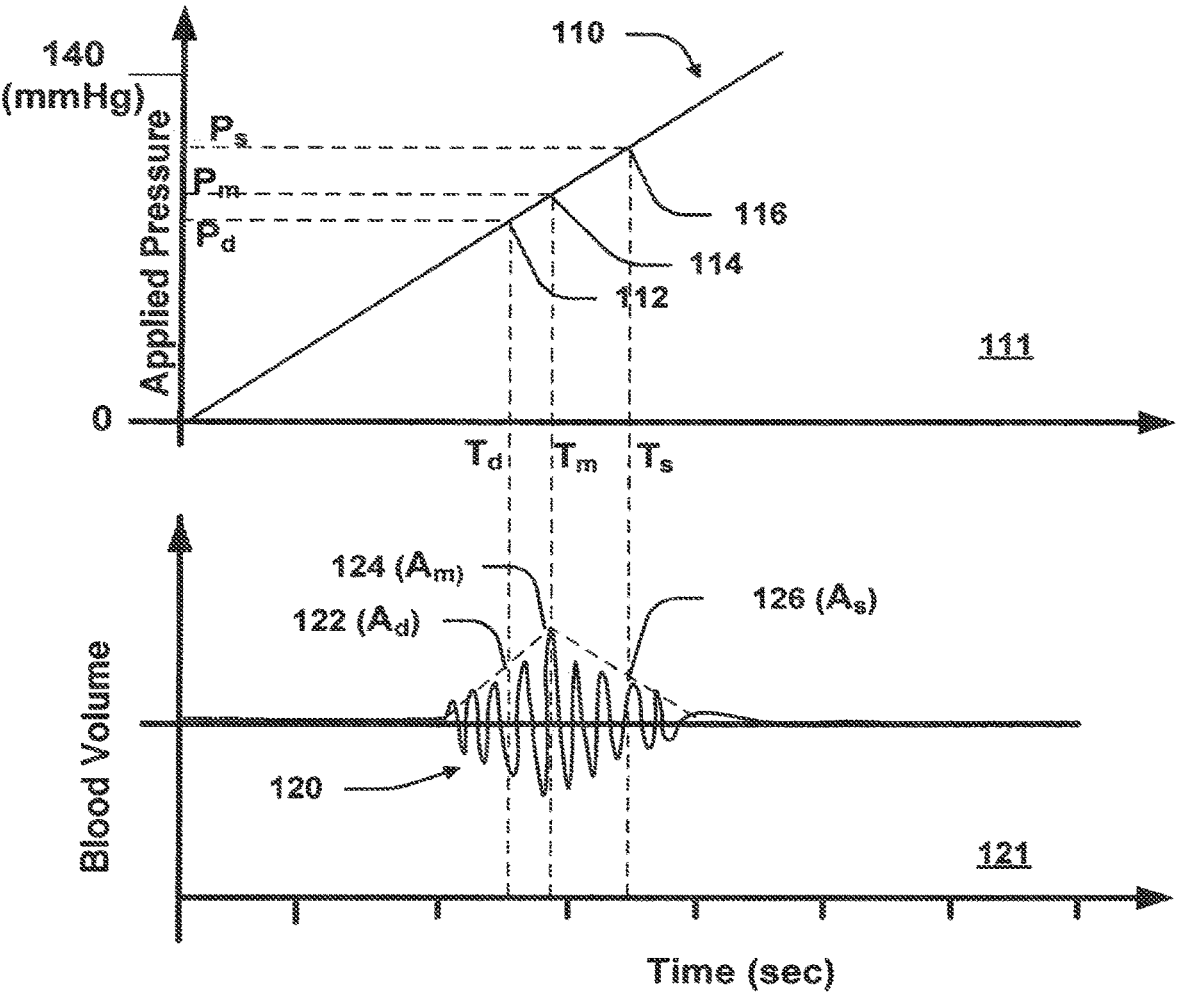
FIG. 1 illustrates how the techniques disclosed herein can exploit the relation between blood pulse amplitude variation and blood pressure to provide estimates of blood pressure.

When an external pressure is applied to the tissue exterior to an arterial blood vessel, an oscillation of the blood vessel (pulsing) occurs only within a certain range of external pressure. The pressure oscillation can be detected and characterized. And relation between the pressure oscillation and blood pressure can be empirically estimated. FIG. 1 illustrates how oscillometric techniques, as well as the techniques disclosed herein, can exploit the relation between blood pulse amplitude variation and blood pressure to provide estimates of blood pressure. The top panel of FIG. 1 shows external pressure data 100 applied to the external tissue of a blood vessel (e.g., an artery or capillary bed). In certain embodiments, the external pressure is generated by the user manually applying force to a portion of the wrist or to a finger. Shown on the horizontal axis is time in seconds and on the vertical axis is pressure in mm Hg. As the external pressure increases and becomes closer to the diastolic and systolic blood pressures, the blood vessel(s) to which the external pressure is applied exhibits detectable variations the amplitudes of the pulses as shown in the lower panel. The illustration of the oscillation is exaggerated and simplified in the figure.

The top panel of FIG. 1 shows the externally applied pressure ramp 110 that causes the variation in pulse amplitude. The bottom panel of FIG. 1 shows the corresponding blood pulse amplitude variation. The blood pulse data 120 ramps up then down in amplitude. It reaches its maximum amplitude $A_m$ at $T_m$, at point 124, corresponding to point 114 when the external pressure equals the mean arterial pressure $P_m$. As the external pressure increases and approaches $P_m$, the pulse amplitude increases and reaches maximum amplitude at $P_m$. Thereafter, as the external pressure continues to increase, the pulse amplitude decreases. The amplitude of the pulses and its relation to the diastolic pressure and the systolic pressure can be empirically determined. For instance, some empirical algorithm identifies the diastolic pressure $P_d$ at point 112 (blow $P_m$) corresponding to an amplitude of the oscillation at $A_d$ at point 122 before it reaches $A_m$, such that $A_d/A_m$ equals 0.85. Some empirical algorithm identifies the systolic pressure $P_s$ at point 116 (above $P_m$) as corresponding to an amplitude of the oscillation at $A_s$ at point 126 after it reaches $A_m$, such that $A_s/A_m=0.55$. Other algorithms may be empirically derived to estimate diastolic pressure and systolic pressure. Various implementations of the current disclosure exploit the relation between blood pressure and oscillation signal.

The pressure applied to the blood vessels during acquisition of blood volume pulses can be obtained in various ways. In many embodiments, the force applied by the user against the underlying blood vessels is measured. If the area of the applied force is constant during the variation in the applied force, the applied pressure is directly proportional to the applied force. In cases where the area of the applied force varies with the applied force, a mechanism for determining the area of application or otherwise determining a relationship between applied force and applied pressure is required. A few examples of techniques for determining the area and/or such relationship are described herein. In one example, the blood pressure measurement device includes a pressing structure having a fixed area that pushes against blood vessels when the user applies force. In another example, a force sensor such as a pressure sensitive pixelated screen is configured to determine not only the total force applied by the user to the pressure sensitive screen but the area of the screen over which the user applies pressure.

In some measurements, the user applies force in a monotonically increasing (or decreasing) manner. In such cases, the pulse amplitude data is correctly ordered with respect to time. However, the user might not always apply steadily increasing or decreasing force. For example, the user may at first increase force, and then decrease force, and finally increase force again. In such cases, the blood pulse amplitude progression typically will not appear as it does in the lower panel of FIG. 1. However, to properly estimate blood pressure from pulse amplitude data, the pulse amplitude data should be provided as a function of increasing (or decreasing) applied external pressure. In cases where the user does not apply force in the same direction, the time varying pulse amplitude values might need to be reordered with respect to pressure in order to facilitate calculating systolic and/or diastolic blood pressure. One way to accomplish this is recognizing that collected data points may include coordinates of pressure (or force), blood volume (or pulse amplitude), and time. The data points are then ordered by ascending (or descending) pressure.

In some implementation, the system can estimate a user's systolic blood pressure by simply determining the pressure at which blood flow occlusion occurs or drops below a threshold (as external pressure increases or decreases). Thus, rather than fitting an envelope to the blood pulse data, the system may simply determine the applied pressure at which the blood flow amplitude first goes to zero or reaches. In such implementations, the blood pressure estimation system may instruct the user to load the user's finger/wrist until the heart beat signal disappears (or its amplitude drops below a predefined level; i.e., blood flow is obstructed), then instruct the user to release the load gradually until the heart beat signal reappears. The load at which the signal reappears (or increases beyond a threshold) is correlated to systolic blood pressure. In general, the pressure at which a PPG waveform becomes apparent (above a threshold) is correlated to the systolic pressure. The pressure at which the PPG waveform disappears (below a second threshold) is correlated to the diastolic pressure.

Certain embodiments pertain to biometric monitoring devices for measuring or estimating a user's blood pressure. In some embodiments, such device includes (a) a wearable fixing structure configured to attach to a user and/or a user's apparel in a manner allowing the user to wear the biometric monitoring device while performing activities, (b) a blood pulse amplitude sensor configured to measure pulses of blood pressure, force, electrical impedance, and/or volume and provide data representing blood pulses of variable amplitude, (c) a force or pressure sensor located and oriented with respect to the blood pulse amplitude sensor to generate variable force or pressure data when a user wearing the fixing structure presses the blood pulse amplitude sensor against a location of the user's body where the blood pulse amplitude sensor generates the blood pulse amplitude sensor data, and (d) one or more processors configured to (i) obtain the blood pulse amplitude sensor data from the blood pulse amplitude sensor, (ii) obtain the variable force or pressure data from the force or pressure sensor, (iii) determine, from the blood pulse amplitude sensor data and the variable force or pressure data, a variation of blood pulse amplitude with a variation in pressure applied to the location where the blood pulse amplitude sensor presses against the user's body, and (iv) determine an estimate of the user's blood pressure from the variation of blood pulse amplitude with variation in applied pressure to the location where the blood pulse amplitude sensor presses against the user's body.

The wearable fixing structure may take many forms. Typically, though not necessarily, the wearer is the user whose blood pressure is being estimated. Some examples of fixing structures are presented in the Appendix below. In various embodiments, the wearable fixing structure takes the form of a band or other engaging structure that wraps around one of the wearer's appendages such as a wrist, ankle, finger, toe, torso, neck, upper arm, waist, etc. The structure may wrap fully or partially around the appendage. Further, the structure may include an enclosure or other associated structure that holds and/or encloses one or more other features of the device, including the sensors, a display, etc. In some embodiments, the wearable fixing structure takes a form that attaches to the wearer's apparel. Examples of such structures include clasps, clips, rings, snaps, zippers, and the like, any of which may include an enclosure or other associated structure that holds and/or encloses one or more other features of the device, including the sensors, a display, etc. Typically, the wearable fixing structure and associated sensors are configured to attach to a user and/or a user's apparel in a manner allowing the user to wear the biometric monitoring device while performing activities. Such activities include both vigorous activities and sedentary activities. A few examples include running, bicycling, swimming, climbing, skiing, weight lifting, boxing, martial arts, gardening, desk work, resting, and sleeping.

In some embodiments, blood pulse and force or pressure sensor data is obtained from an appendage where the user wears the fixing structure. For example, a wrist worn fixing structure may operate to capture the user's heart beat pulse amplitude from blood vessels in the user's wrist. Similarly, and ankle worn fixing structure may operate to capture the user's heart beat pulse amplitude from blood vessels in the user's ankle. In such embodiments, the blood pulse amplitude sensor is oriented and located to obtain relevant physiological signals (e.g., blood volume) from the tissue of the user's appendage on which the fixing structure is worn. To this end, some pulse amplitude sensors are oriented and configured with respect to the fixing structure so that they direct light or other probe into or toward the appendage or other location on which the fixing structure is worn. The particular blood vessels from which the blood pulse amplitude data is obtained depends on the location of the blood pulse amplitude sensor with respect to the fixing structure, and consequently with respect to the user's appendage. For example, a blood pulse amplitude sensor located on the back of the user's wrist may obtain blood pulse amplitude data from a capillary bed on the back of the user's wrist, while a blood pulse amplitude sensor located on the front of the user's wrist (palm side) may obtain blood pulse amplitude data from a radial artery on the user's wrist.

In some embodiments, blood pulse and force or pressure sensor data is obtained from a first location on the user's body, while the fixing structure is worn a second location of the user's body, which is different from the first location. For example, the user may wear the fixing structure (and associated sensors) on her left wrist, while obtaining the blood pulse amplitude data from her right index finger or neck. In such example, the user pushes her right finger against a portion of the biometric device holding the sensors or pushes the sensors against her neck by, for example, pushing a sensor containing portion of the wrist worn device against her neck. In such embodiments, the blood pulse amplitude sensor is oriented and located to obtain relevant physiological signals (e.g., blood volume) from the tissue that is separated from the location wear the user wears the fixing structure. Therefore, some pulse amplitude sensors must be oriented and configured with respect to the fixing structure so that they direct light or other probe away from the appendage or other location on which the fixing structure is worn.

In certain implementations, the blood pulse amplitude sensor is a photoplethysmogram (PPG) sensor including a light emitter and a light detector configured to generate PPG sensor data. While most of this document describes PPG sensing and the use of blood volume pulses to determine internal blood pressure, the disclosed embodiments are not limited to PPG sensing or blood volume measurements. Many other pressure sensitive techniques for measuring blood pulse amplitude may be used to estimate blood pressure in accordance with embodiments of this disclosure. In certain implementations, the blood pulse amplitude sensor is a bioelectrical impedance analysis (BIA) sensor or a ballistocardiograph (BCG) sensor. Unless otherwise stated or clear from context, references to PPG sensors and sensor data apply equally other types of blood pulse amplitude sensors and data therefrom.

The force or pressure sensor is generally located to register external force or pressure applied by the user when she pushes the blood pulse amplitude sensor against the location on her body from which the blood pulse amplitude sensor obtains the blood pulse amplitude data. Thus, for example, the force or pressure sensor may be located on an axis defined by a signal capture portion of the blood pulse amplitude sensor and the blood vessel(s) from which such signal is captured. Along such axis the force or pressure sensor may be sandwiched between the blood vessel(s) and blood pulse amplitude sensor or may be located outside the blood vessel(s) and the amplitude sensor, such that the amplitude sensor is sandwiched between the blood vessel(s) and the force or pressure sensor. In general, the force or pressure sensor is located close to the signal capture portion of the blood pulse amplitude sensor, with typically less than about 1 centimeter separating them; e.g., less than 5 millimeters separation, or less than about 2 millimeters separation.

In some embodiments, the one or more processors are incorporated in a single structure with the sensors and the wearable fixing structure. For example, the fixing structure may include one or more enclosures, slots, clips, etc. that hold the processor(s) and sensors. In other embodiments, at least one of the one or more processors is located off the wearable fixing structure. In such embodiments, a processor or processors may be provided on a secondary device such as a smart phone, a personal computer (e.g., a laptop or tablet), or a server. The server may be provided on a private network or the Internet. In the latter case, the server may be a server farm, or a part thereof, and may be leased or otherwise provided as a service on the "cloud." In certain embodiments, the biometric monitoring device includes a wireless transmitter configured to transmit the blood pulse amplitude data (e.g., PPG sensor data) and the variable force and/or pressure data to a remote device. Further, at least one of the one or more processors may be located in the remote device.

The one or more processors are typically integrated circuits, which may be general purpose integrated circuits or custom designed (or optimized) integrated circuits such as digital signal processors. The processor(s) may operate under the control of program instructions including, for example, machine code and/or microcode stored on memory available to the processor(s) or embedded in the processor as, for example, firmware. As examples, the memory include volatile memory such as random access memory (DRAM or SRAM) or non-volatile memory such as read only memory (ROM), EPROM, flash memory, and the like. Some or all of the memory may be disposed on the same integrated circuit that executes the instructions. Thus, in some embodiments, some or all of the memory may be considered to be included in the processor(s).

FIG. 2 presents a flow chart of operations that may be performed by the one or more processors to estimate a user's blood pressure. In the depicted process 201, the processor(s) obtain blood pulse amplitude sensor data from the blood pulse amplitude sensor. See block 203. As an example, the blood pulse amplitude data may be data representing optical signals from a photodetector of a PPG sensor, which optical signals correspond to blood volume in blood vessels probed by light pulses emitted by the PPG sensor. In another example, the blood pulse amplitude data is impedance data from a BIA sensor configured and oriented to detect impedance variations caused by blood flow variations through blood vessels having significant impact on the impedance detected by the sensor. In still another example, the blood pulse amplitude data is force data from a BCG sensor configured and oriented to detect force variations caused by blood flow variations through blood vessels having significant impact on the force values detected by the sensor. The BCG sensor may employ a piezoelectric element to detect force variations caused by nearby blood flow variations.

Returning to the process flow 201, the processors also obtain variable force or pressure data from the force or pressure sensor as depicted in block 205. This data may represent the output of electrical signals captured by a piezoelectric element or other element of the sensor that responds to force or pressure variations. As explained, the force or pressure sensor may be a force sensitive touch screen, a strain gauge, or force sensing button, and the like. In some embodiments, the processor(s) or other processing logic receives a force sensor's output and converts to data representing pressure applied to the user's blood vessels resulting from the user pressing the pulse amplitude sensor against the blood vessels.

The sensor data obtained in operations 203 and 205 may be obtained directly and/or indirectly from the sensors. In some embodiments, the sensor data is stored temporarily on memory in the biometric monitoring device or another device before being provided to (or taken by) the one or more processors. In some embodiments, the data is provided directly to the processor(s) where the data is optionally stored in one or more buffers. In some embodiments, the output of the blood pulse amplitude sensor and/or the force or pressure sensor is first manipulated to become the data provided to the one or more processor(s). For example, the data may be scaled, normalized, filtered, etc. before being provided to or used by the processor(s). These actions may be performed by a peripheral logic on the processor(s) or by separate logic incorporated in the sensors or elsewhere. The data from both the blood pulse amplitude sensor and the force or pressure sensor is provided with time information (e.g., timestamps) which allows the pulse amplitude data to be directly linked to force or pressure data that results in the detected pulse amplitudes. In some cases, the user does not apply external pressure in a consistent manner. In such cases, the one or more processors may be further configured to order the amplitudes of the blood volume pulses from the blood pulse amplitude data so that the amplitudes vary with pressure caused by the user pressing the pulse amplitude sensor against the location of the user's body where the sensor generates the pulse amplitude sensor data.

In certain embodiments, the sensor data is processed in real time, to provide the results of operations 207 and/or 209; that is, the time between when the sensor data is received in operations 203 and 205 and when the data is analyzed to the results of operations 207 and/or 209 is very short; e.g., on the order of a second or less, or a microsecond or less, on a millisecond or less. Operations 203 and 205 may be performed at substantially the same time or one may be performed prior to the other.

Next, in the depicted process 201, the one or more processors determine, from the blood pulse amplitude sensor data and the variable force or pressure data, a variation of blood pulse amplitude with a variation in pressure applied to the location where the blood pulse amplitude sensor presses against the user's body. See block 207. As explained, the variation of blood pulse amplitude with variation in external pressure applied to the user's blood vessels contains information useful for determining the user's systolic and/or diastolic blood pressure. In some embodiments, the one or more processors use the pulse amplitude sensor data and the variable force or pressure data to determine the pressure at which the user's blood vessels first become occluded. This is the pressure at which the pulse amplitude is no longer detectable. This pressure also allows the one or more processors to determine the user's systolic blood pressure.

Finally, in the depicted process 201, the one or more processors determine an estimate of the user's blood pressure from the variation of blood pulse amplitude with variation in applied pressure to the location where the blood pulse amplitude sensor presses against the user's body. In certain embodiments, this estimate is obtained using well-known techniques such as those employed in oscillometric techniques and alluded to in the discussion of FIG. 1. Also, as just mentioned, the one or more processors may be configured to determine the user's systolic blood pressure from the external pressure at which the pulse amplitude is no longer detectable.

In certain embodiments, the biometric monitoring device tracks the user's activity and uses activity type and/or activity level in determining whether to estimate blood pressure or how to estimate blood pressure. For example, a biometric monitoring device may detect that a user just completed an exercise and based on that, determine that is should not take a blood pressure reading or use a more stringent algorithm blood pressure estimation. This approach may be appropriate when the activity type or activity level is known produce a blood pressure reading that would likely be inaccurate.

First Embodiments (Biometric Monitoring Device)

In these embodiments, a biometric monitoring device is worn on or attached to (directly or indirectly) a first location of wearer and used to measure the blood pulse amplitude at a second location, which is different from and separated from the first location. In fact, the second location may be on an individual other than the wearer, although in many cases, the first and second locations are on the body of the same individual. In some cases, the pulse amplitude sensor is oriented with respect to the wearable fixing structure such that when the user wears the biometric monitoring device, the light emitter directs light toward a portion of the user's body on which the biometric monitoring device is not worn. The location of the user's body where the blood pulse amplitude sensor generates the pulse amplitude sensor data is the portion of the user's body on which the device is not worn. In some cases, the wearable fixing structure is configured to be worn on the user's wrist and the location of the user's body where the PPG sensor generates the PPG sensor data is a digit of the user such as the user's index finger.

In certain embodiments of this section, the second location, the blood flow pulse amplitude sensor, and the force or pressure sensor are located substantially along a single axis or column. When the wearer pushes against the biometric monitoring device at the location of the pulse amplitude sensor, the force or pressure provides data reflecting the wearer's applied force or pressure, and the pulse amplitude sensor provides data reflecting the pulse amplitude of one or more blood vessels at the second location.

Figure 3A:
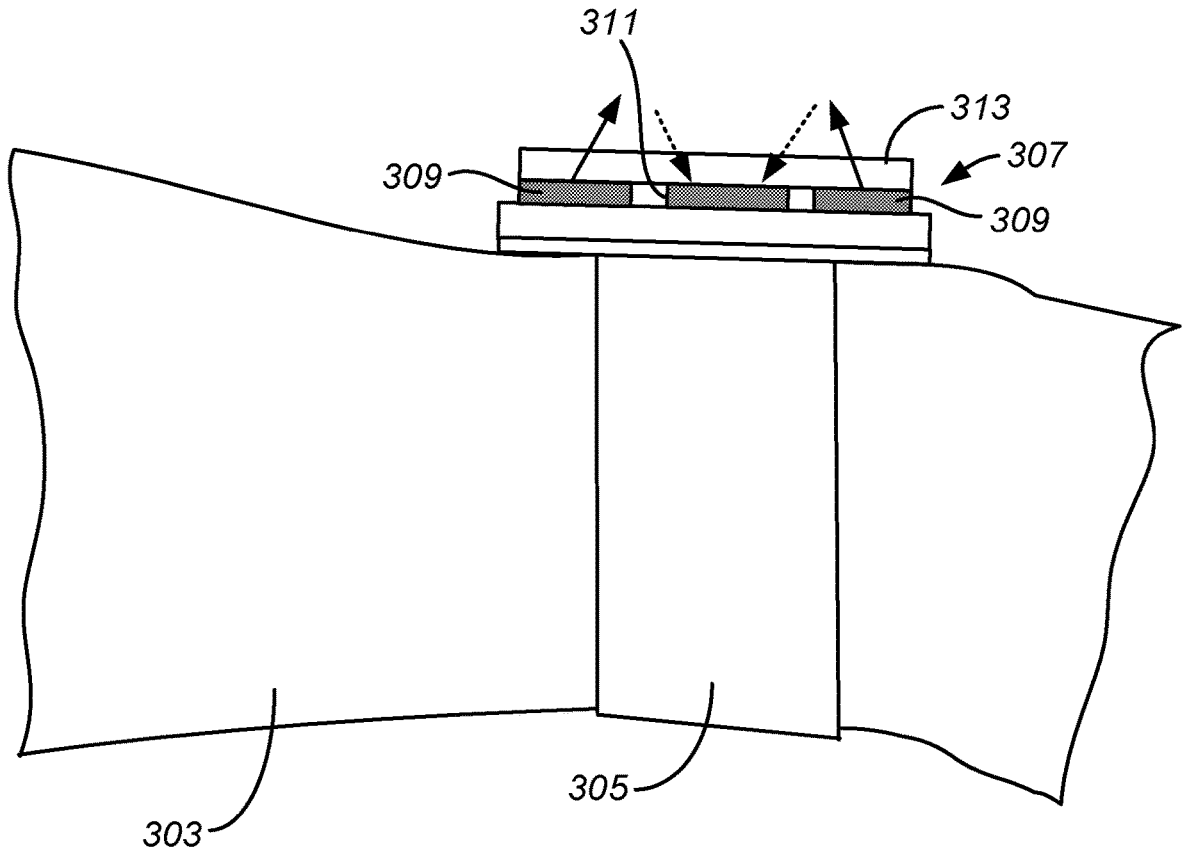
FIG. 3A depicts a worn biometric monitoring device for receiving blood pulse amplitude data from a side of the device that faces away from the portion of user's body on which the device is worn.

In some embodiments, the pressure or force sensor is a force sensitive display screen. In these or other embodiments, the blood pulse amplitude sensor is a PPG sensor. In these or other embodiments, the force sensitive display screen is located outwardly from the blood pulse amplitude sensor. In other words, the pulse amplitude sensor is closer than the screen to the first location on the user. Such embodiment is depicted in FIG. 3A. In alternative embodiments, a force or pressure is closer than the pulse amplitude sensor to the first location. In either approach, the force or pressure sensor need not be a force sensitive display screen.

FIG. 3A depicts a biometric monitoring device on a user's wrist or other appendage 303. The biometric monitoring device includes a wrist band 305 (which could be another type of wearable structure), a PPG sensor 307, and a force sensitive display screen 313, which may be a touch screen. The PPG sensor includes two light emitters 308 (e.g., LEDs) and a light detector 311 (e.g., a photodetector such as a photodiode or a charge coupled device). In certain embodiments, only a single light emitter is employed. In other embodiments, three or more emitters are employed. As depicted, light emitted from emitters 309 passes upward (away from the user's wrist) and through display screen 313. See the solid arrows. The light then interacts with blood vessels at the second location on the user, where it is modified to a degree that is influenced by the current blood volume in the blood vessels at the second location. The modified light is directed back toward PPG sensor 307 by reflection and/or refraction. See the dashed arrows. The modified light is then detected by detector 311, which generates data reflective of the current blood volume of the blood vessels at the user's second location.

In one embodiment, the biometric monitoring device includes (a) a wearable fixing structure in a wrist wearable form factor, (b) a display with a force-sensitive screen, and (c) a PPG sensor that is configured to transmit light through the display toward the user's second location. In one use case, the user presses a side of her finger 317 against the screen to expose the radial artery to the PPG emitted light. See FIG. 3B. In some implementations, the user presses the tip of her finger against the display screen, in which case the capillary bed in the fingertip provides the blood volume reflective data.

In certain embodiments, the light emitter of the PPG sensor emits light outside the visible portion of the electromagnetic spectrum. Such light emitter may be an infrared light emitter. In such embodiments, the light from the PPG sensor will not interfere with the user's viewing of the display screen.

In some embodiments, the PPG sensor's light emitter is a display screen. For example, a pixelated display screen may be operated (under the direction of the processors) to emit light pulses of wavelength, intensity, duration, periodicity, duty cycle, numerical aperture, direction, etc. suitable to generate blood pulse amplitude data at a photo detector.

In some examples, the biometric monitoring device additionally includes a capture structure configured to engage the side of the user's index finger when the PPG sensor generates the PPG sensor data from the user's index finger. In some examples, a capture structure is configured to engage the tip of the user's index finger when the PPG sensor generates the PPG sensor data from the user's index finger.

Figure 3B:
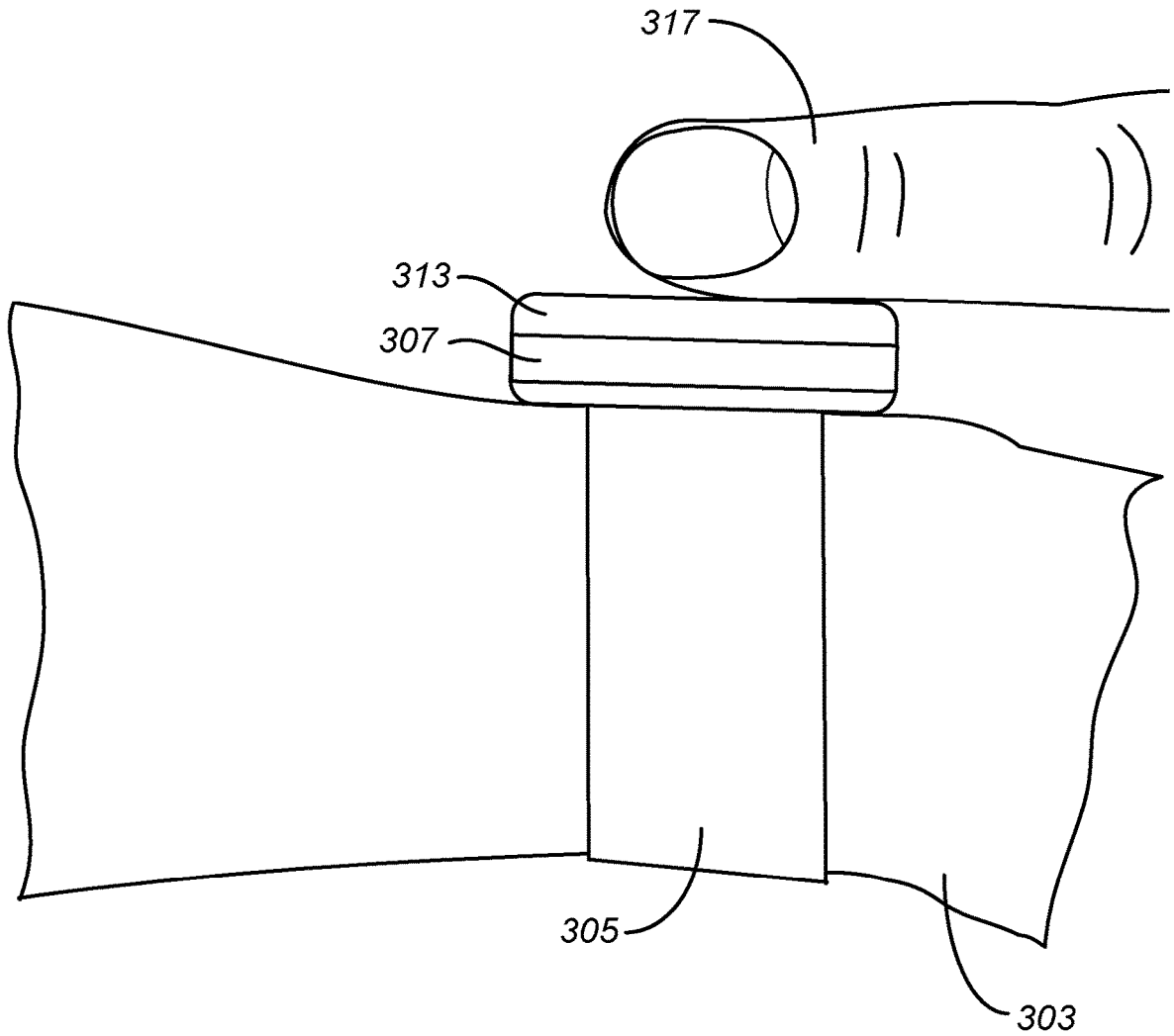
FIG. 3B depicts a digit placed against the back side of biometric monitoring device. Blood pulse amplitude data is obtained from the digit.
Figure 3C:
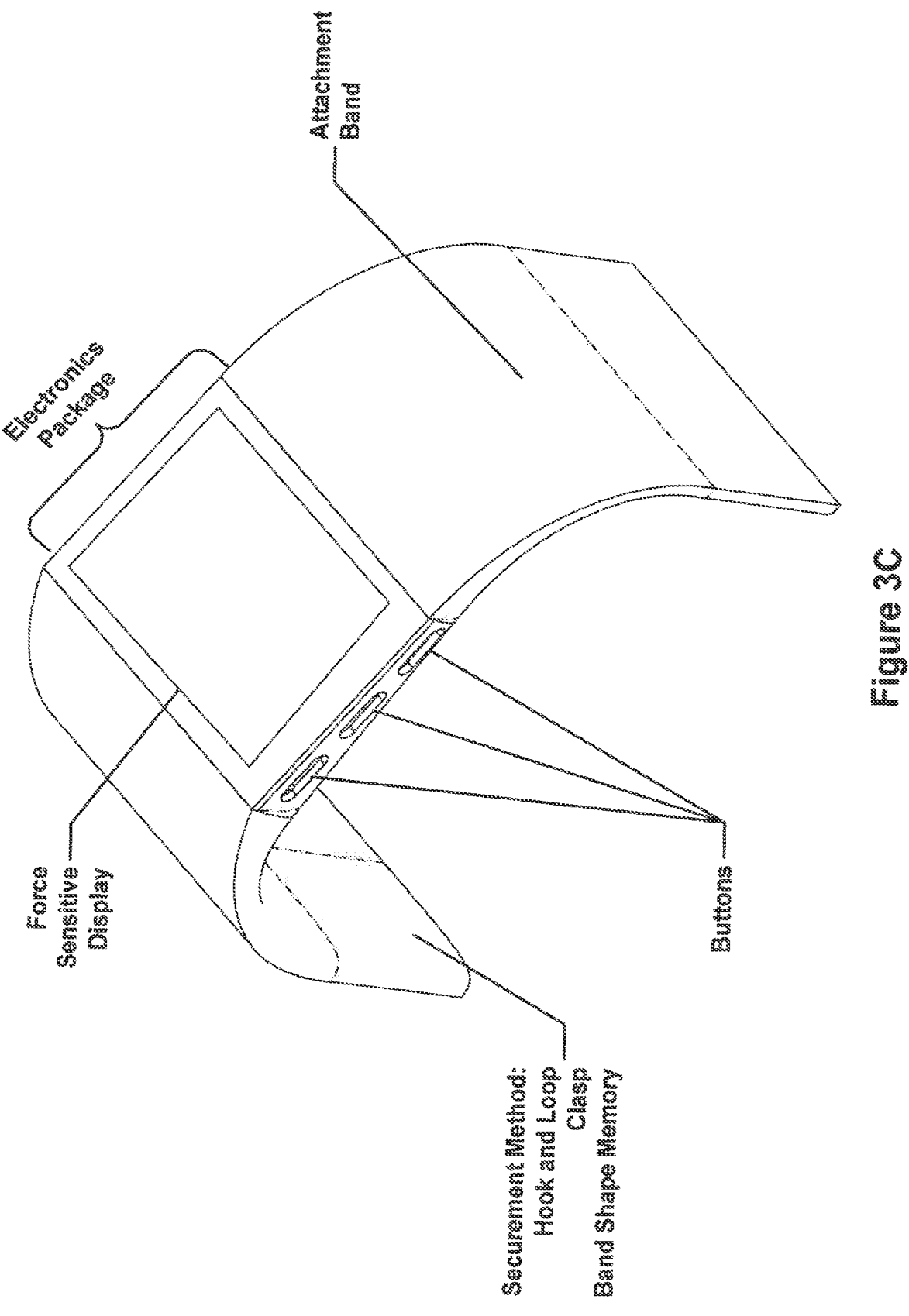
FIG. 3C shows an example of biometric monitoring device.

A further example of a wrist-worn portable biometric monitoring device is shown in FIG. 3C. This device may have a touch sensitive display screen, button(s), electronics package, and/or an attachment band. A blood pulse amplitude sensor is disposed beneath the display screen (closer to the user's wrist). The attachment band may be secured to the user through the use of hooks and loops (e.g., Velcro), a clasp, and/or a band having memory of its shape, e.g., through the use of a spring metal band.

Portable biometric monitoring devices such as those described herein for estimating blood pressure may collect one or more types of physiological and/or environmental data from embedded sensors and/or external devices and communicate or relay such information to other devices, including devices capable of serving as an Internet-accessible data sources, thus permitting the collected data to be viewed, for example, using a web browser or network-based application. For example, while the user is wearing a biometric monitoring device, the biometric monitoring device may—in addition to obtaining sensor data for estimating blood pressure—calculate and store the user's step count using one or more biometric sensors. The biometric monitoring device may then transmit data representative of the user's step count to an account on a web service (e.g., www.fitbit.com), computer, mobile phone, or health station where the data may be stored, processed, and visualized by the user. Indeed, the biometric monitoring device may measure or calculate a plurality of other physiological metrics in addition to, or in place of, the user's step count and/or blood pressure. These include, but are not limited to, energy expenditure, e.g., calorie burn, floors climbed and/or descended, heart rate, heart rate variability, heart rate recovery, location and/or heading, e.g., through GPS, GLONASS, or a similar system, elevation, ambulatory speed and/or distance traveled, swimming lap count, swimming stroke type and count detected, bicycle distance and/or speed, blood pressure, blood glucose, skin conduction, skin and/or body temperature, muscle state measured via electromyography, brain activity as measured by electroencephalography, weight, body fat, caloric intake, nutritional intake from food, medication intake, sleep periods, e.g., clock time, sleep phases, sleep quality and/or duration, pH levels, hydration levels, respiration rate, and other physiological metrics. The biometric monitoring device may also measure or calculate metrics related to the environment around the user such as barometric pressure, weather conditions (e.g., temperature, humidity, pollen count, air quality, rain/snow conditions, wind speed), light exposure (e.g., ambient light, UV light exposure, time and/or duration spent in darkness), noise exposure, radiation exposure, and magnetic field. Furthermore, the biometric monitoring device or the system collating the data streams from the biometric monitoring device may calculate metrics derived from such data. For example, the device or system may calculate the user's stress and/or relaxation levels through a combination of heart rate variability, skin conduction, noise pollution, and sleep quality. In another example, the device or system may determine the efficacy of a medical intervention, e.g., medication, through the combination of medication intake, sleep data, and/or activity data. In yet another example, the biometric monitoring device or system may determine the efficacy of an allergy medication through the combination of pollen data, medication intake, sleep and/or activity data. These examples are provided for illustration only and are not intended to be limiting or exhaustive. Further embodiments and implementations of sensor devices may be found in U.S. Pat. No. 9,042,971, titled "Biometric Monitoring Device with Heart Rate Measurement Activated by a Single User Gesture" and filed on Jan. 13, 2014, U.S. Pat. No. 9,044,149, titled "Pulse waveform data Collection" and filed on May 29, 2014, U.S. Pat. No. 8,948,832, titled "Wearable Pulse waveform monitor or heart rate monitor" and filed on May 30, 2014, U.S. patent application Ser. No. 13/156,304, titled "Portable Biometric Monitoring Devices and Methods of Operating Same" filed on Jun. 8, 2011 and U.S. Patent Application 61/680,230, titled "Fitbit Tracker" filed Aug. 6, 2012, which are hereby incorporated herein by reference in their entireties.

Second Embodiments (Biometric Monitoring Device)

In these embodiments, the biometric monitoring device is configured such that the PPG sensor (or other blood pulse amplitude sensor) is oriented with respect to the wearable fixing structure such that when the user wears the biometric monitoring device, the light emitter directs light toward a portion of the user's body on which the biometric monitoring device is worn. The location of the user's body where the blood pulse amplitude sensor generates the pulse amplitude sensor data is the portion of the user's body on which the device is worn. In certain embodiments, the portion of the user's body on which the device is worn by the user is the user's wrist. In such cases, the wearable fixing structure may include a wrist band, and the PPG or other blood pulse amplitude sensor and/or the force or pressure sensor may be disposed in the wrist band. In one embodiment, the light emitter of a PPG sensor is oriented to emit light into the back of the user's wrist when the user wears the biometric monitoring device. In some implementations, the user presses the device against the wrist with an opposing finger to actuate the forces applied to the back of the wrist's capillary bed. The force or pressure sensor in the device measures the actuation of the user. In some embodiments, the light emitter of PPG sensor is oriented to emit light into the palm side of the user's wrist, proximate a pulse point on the user's wrist, when the user wears the biometric monitoring device. Otherwise, the device may be designed and used in a manner similar to that of the wrist backside implementation.

The force/pressure sensor may be integrated into the top surface of the device (e.g., a force sensitive touch screen or force sensitive film), a strain gauge designed into the housing, or a calibrated spring element (e.g., button) that the user presses. Notably, these elements may instead be designed into the bottom housing (e.g., a protrusion housing elements of a PPG sensor or other blood pulse amplitude sensor).

Some biometric monitoring devices of this section may have a structure similar to that of FIGS. 3A and 3B but the direction of the PPG sensor's light emitters and detector is reversed, so that the PPG sensor collects blood volume data from blood vessels in the user's wrist or other appendage on which the biometric monitoring device is worn. Notably, and not shown in FIGS. 3A and 3B, the PPG sensor components (particularly the emitter(s) and detector) may be part of a protrusion that extends inwardly toward the user's appendage, away from the exterior. Example embodiments with such protrusions are depicted in figures later in this disclosure. The protrusions have a defined area, which may be useful in determining user-applied pressure from measurements of user-applied force.

Figure 4A:
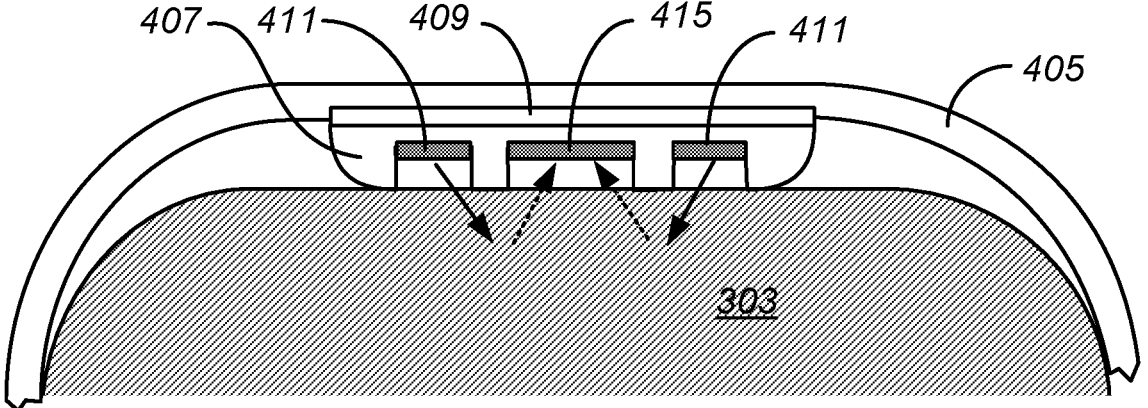
FIG. 4A depicts a worn biometric monitoring device for receiving blood pulse amplitude data from a side of the device that faces toward the portion of user's body on which the device is worn.

FIG. 4A depicts a biometric monitoring device embodiment in which a PPG sensor including light emitters 411 and light detector 415 is oriented and located to direct light into blood vessels on the user's appendage 303. See the solid arrows. The PPG sensor components are includes in a rigid protrusion 407, which is attached to a wearable fixing structure 405 (e.g., a wrist band). Between the PPG sensor components the exterior of wearable structure 405 is a force sensor 409, which may be a strain gauge, a force sensitive film, a force sensitive screen, etc. When the user presses against the back of the wearable structure 405 to push protrusion 407 into the user's wrist, the force sensor 409 generates data indicative of the applied force and PPG detector 415 generates data indicative of blood volume (in response to light returning from the blood vessels as indicated by the dashed arrows).

Figure 4B:
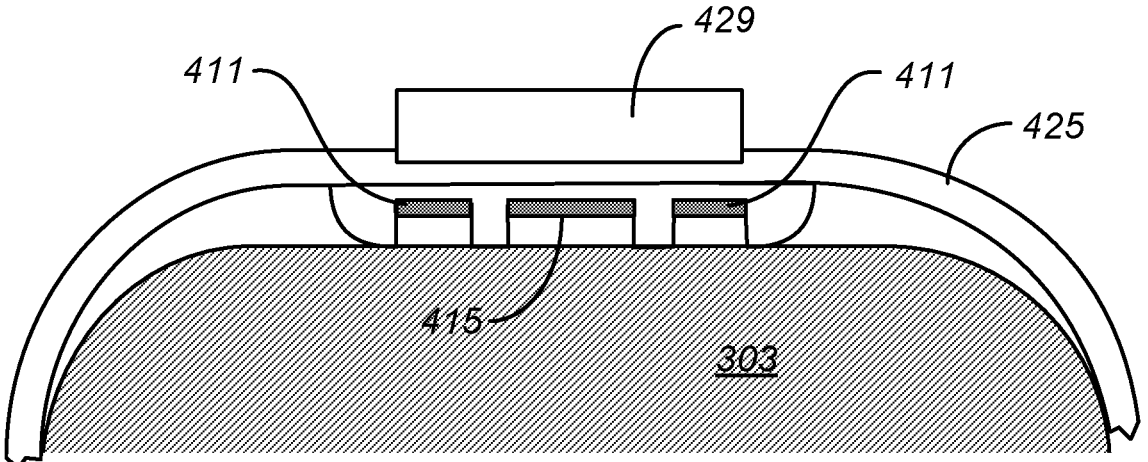
FIG. 4B depicts another version of a worn biometric monitoring device.

FIG. 4B shows an embodiment similar to that of FIG. 4A except that the force sensor 409 is replaced by a force sensing button 429 located on the upper (outer) side of the wearable fixing structure 425. When the user pushes on button 429, the internal sensing mechanism (e.g., a calibrated spring and displacement detecting mechanism) generates data indicative of the user's applied force. Concurrently, the PPG photo detector 415 generates data indicative of blood volume in nearby blood vessels of the user's appendage (e.g., wrist).

Force Sensing

As explained, the biometric monitoring devices include a force or pressure sensor. In some embodiments, such sensor is a force sensor that is a force sensitive display screen such as touchscreen. In some implementations, the force sensitive display screen includes a piezo resistive pixelated touch sensitive display, which generates the variable force data when a user wearing the fixing structure presses the blood pulse amplitude sensor (e.g., a PPG sensor) against the location of the user's body where the pulse amplitude sensor generates the pulse amplitude sensor data. In some embodiments, the display screen includes pixels having variable density (number of pixels per unit touch area). In some examples, the display screen has a greater density of pixels in a region where the user is expected to apply pressure than in a region where the user is less likely to apply pressure. For example, the display screen may have a greater pixel density in a center region than in a peripheral region. A force sensitive display screen may have other roles in the estimation of blood pressure. For example, it may be configured to display instructions to the user such as instructions to apply force, apply greater force, apply less force, etc. It may also be configured to display biometric information such as step count and other types of biometric information described herein, including blood pressure data. Of course, the one or more processors may provide the control (instructions and data) to cause such information to be displayed. Also, as mentioned, a force sensitive display screen may be configured (along with the processor(s)) to emit light pulses and thereby serve as part of a PPG sensor.

In certain embodiments, the force or pressure sensor includes a strain gauge, a button, and/or a spring.

In certain embodiments, the one or more processors and/or the touch sensitive display are configured to dynamically oversample an area of the touch sensitive display detected to be in contact with the location of the user's body where the PPG sensor generates the PPG sensor data.

DETERMINING APPLIED PRESSURE FROM APPLIED FORCE

Often it the biometric monitoring device includes only a force sensor (no pressure sensor), but the blood pressure estimate relies on pressure values. Pressure is equal to force divided by area, but the contact area of the finger/wrist is, in many embodiments, not well controlled. For example, as a user presses harder, the contact area may increase.

In certain embodiments, the biometric monitoring device includes a force sensor and logic (as implemented in the one or more processors) to convert force sensor generated data to pressure values. Such logic may be designed or programmed to perform this conversion in various ways, depending on the structure of the device and the available information and data.

In one example, the force sensor output is calibrated against a blood pressure cuff. For example, by establishing the relationship between the force readings from the force sensor and the actual pressure exerted (from the blood pressure cuff). In a related approach, the blood pressure sensor is trained or calibrated using blood pressure estimates made using force data, without directly converting the force data to pressure values, and this estimate is calibrated against a blood pressure values obtained using a blood pressure cuff.

In certain embodiments, the force sensor has a variable area capture device (such as a force sensitive display screen) which can be used to determine a contact area as it varies (e.g., area occupied by pixels sensing user applied force at times 0 through $t_n$). In certain embodiments employing a pixelated force sensitive film or screen (e.g., piezo resistive pixelated touch sensitive display), the one or more processors and/or the pixelated force sensitive display screen is configured to determine pressure produced when the user presses the PPG sensor against the location of the user's body where the PPG sensor generates the PPG sensor data. In such embodiments, the one or more processors and/or the pixelated force sensitive display may be configured to: (a) determine an area occupied by pixels of the touch sensitive display detecting force caused when the user presses the PPG sensor (or other blood pulse amplitude sensor) against the location of the user's body where the PPG sensor generates the PPG sensor data; and (b) determine pressure by using (i) the force data from the touch sensitive display together with (ii) the area occupied by the pixels of the touch sensitive display detecting force caused when the user presses the PPG sensor against the location of the user's body where the PPG sensor generates the PPG sensor data. To facilitate area determination, the touch sensitive display screen may have a pixel density that is greater in a first portion of the display screen than in second portion of the display screen. E.g., a central region of the display may have a greater pixel density. In certain embodiments, the one or more processor(s) and/or the display screen are configured to display a region where the user is expected to apply force with a finger or other portion of the user's body.

In another approach to converting force sensor output data to pressure values, the biometric monitoring device employs a constant area capture device such as a PPG protrusion or a finger shaped structure attached to the biometric monitoring device. In such embodiments, the one or more processors and/or force or pressure sensor is configured to determine pressure produced when the user presses the PPG sensor (or other blood pulse amplitude sensor) against the location of the user's body where the PPG sensor generates the PPG sensor data. The one or more processors and/or force or pressure sensor may be configured to determine the pressure using (a) force detected by the force or pressure sensor, and (b) an area of a capture structure on the biometric monitoring device against which the user presses when pressing the PPG sensor against the location of the user's body.

In certain embodiments, the capture structure includes markings defining an area (e.g., a round or elliptical area) intended to accept the location on the user used to press against the sensors. In embodiments where the user is to press against a flat surface like a force sensitive display, the device (through its processor(s)) can control the display by marking out the area for the user to apply the finger or other body feature. In certain embodiments, the marking is a ring or a circle.

PPG Sensing and Other Pulse Amplitude Measurement Technologies

In certain embodiments employing a PPG sensor as the blood pulse amplitude sensor, the PPG sensor's light emitter and the force or pressure sensor are oriented such that when the light emitter emits light for generating the PPG sensor data, the light passes through the force or pressure sensor. In such cases, the force or pressure sensor is substantially transparent to the light from the PPG light emitter. Examples of suitable force or pressure sensors include transparent strain gauges and transparent forces sensitive screens and films.

In certain embodiments employing a PPG sensor as the blood pulse amplitude sensor, the PPG sensor is oriented with respect to the wearable fixing structure such that when the user presses the PPG sensor against the location of the user's body, the PPG sensor generates PPG sensor data representing blood volume pulses of a capillary bed proximate the location of the user's body. In certain embodiments employing a PPG sensor as the blood pulse amplitude sensor, the PPG sensor is oriented with respect to the wearable fixing structure such that when the user presses the PPG sensor against the location of the user's body, the PPG sensor generates PPG sensor data representing blood volume pulses of an artery proximate the location of the user's body.

As mentioned, blood flow pulse amplitude sensor may be sensor other than PPG sensor, such as one that outputs data responsive to changes in local impedance, force, pressure, voltage, etc. resulting from changes in blood pulse pressure amplitude. Examples of such sensors include BCG sensors, BIA sensors, and the like.

In certain embodiments, the one or more processors and/or the blood pulse amplitude sensor are configured to determine a user's heart rate from blood pulse data obtained using the sensor. Examples of techniques for measuring heart rate using a PPG sensor are known to those of skill in the art and are further described in, for example, U.S. Pat. Nos. 8,954,135, 9,044,149, 8,948,832, and 9,005,129, each of which is incorporated herein by reference in its entirety. In certain embodiments, the PPG sensor's sampling rate for detecting pulse amplitude variations and for detecting heart rate is different. For example, the pulse amplitude variations sampling frequency may be greater.

Providing Feedback or Instructions to Users

In certain embodiments, the biometric monitoring device provides feedback and/or instructions to the user by a visual, auditory, or tactile mechanism such as a display (which may double as a force sensor), a speaker, a vibrator, and the like. In various embodiments, the biometric monitoring device includes a display screen, and the one or more processors are configured to present the instructions to the user via the display screen.

The content of such feedback or instructions depends on the application. In some cases, the content instructs the user on applying force to the blood pulse amplitude sensor to facilitate generating an estimate of blood pressure. For example, the device may instruct the user on when and whether to increase or decrease the applied pressure. In some cases, the content instructs the user on adjusting the height of the PPG sensor to an elevation approximately the same as that of the user's heart.

In certain embodiments, the one or more processors are configured to present instructions to the user to apply force to a location on the biometric monitoring device. Applying force to said location of the biometric monitoring device presses the blood pulse amplitude sensor against the location of the user's body where the pulse amplitude sensor generates the pulse amplitude sensor data. To this end, the one or more processors may be configured to present instructions to the user to press the user's finger against the location on the biometric monitoring device. Further, the one or more processors may be configured to present instructions to the user to vary the force applied to the location on the biometric monitoring device. Still further, the one or more processors may be configured to present instructions to the user to vary the force applied to the location on the biometric monitoring device until a PPG sensor data (or other blood pulse amplitude sensor data) shows that the user's blood volume pulses disappear or appear.

To facilitate providing correct instructions to the user, the one or more processors may determine the level of flat surface on the biometric monitoring device (e.g., a watch face profile) as determined by accelerometers or other devices sensitive to angle with respect to gravity. The processor(s) may be configured to detect when the watch face is substantially horizontal or substantially vertical—the two modes most commonly employed when the user places a wrist worn blood pulse amplitude sensor at the elevation of her heart. When the arm is held at distance away from the heart, the watch face is typically flat. When the arm is held against the chest (near the heart), the watch face is typically vertical.

To facilitate providing correct instructions to the user, the one or more processors may determine detect changes in altitude in response to instructions to move sensor to heart level. The biometric monitoring device may employ an altimeter for this purpose. In certain embodiments, the one or more processors are further configured to present instructions to the user to adjust the position of the user's body location so that the blood pulse amplitude sensor is located at approximately the same elevation as the user's heart. Determining Whether the Pulse Amplitude Sensor is at the Elevation of the User's Heart In certain embodiments, the user is instructed to hold his hand/wrist (or other location having the blood pulse amplitude sensor) to be at approximately the same level as the heart. In a watch form factor, the angle of the watch as determined by the accelerometer assists in determining if the user is holding the correct position. The user is instructed to lower or raise the arm to get to the right angle/level. Simultaneously, an altimeter in the same device may measure the change in elevation in response to changes in angle of the device in order to better instruct the user on how reach the correct level (e.g., "lower your wrist by 2 inches").

In certain embodiments, the one or more processors are configured to present instructions to the user to adjust the position of the user's body location so that the blood pulse amplitude sensor is located at approximately the same elevation as the user's heart. In such embodiments, the biometric monitoring device may additionally include a motion sensor, and the one or more processors may be further configured to use data generated by the motion sensor to determine whether the PPG sensor is located at approximately the elevation as the user's heart. As examples, the motion sensor may be an accelerometer, an altimeter, and/or a gyroscope. In some implementations, the one or more processors are further configured to provide feedback when it is determined that the PPG sensor is located at approximately the elevation of the user's heart.

In certain embodiments, the biometric monitoring device additionally includes a display screen, and the one or more processors are further configured to present the instructions and/or feedback regarding the elevation of the pulse amplitude sensor to the user via the display screen. PTT Calibration Using Blood Pressure Data from the Embodiments 1 and 2

Pulse transit time (PTT) is a useful blood pressure measurement technology but PTT sensing mechanisms typically require frequent recalibration because the relationship between PTT and blood pressure typically varies throughout the day based on user physical activity, eating, etc. Using embodiments 1 or 2 to frequently calibrate the PTT data allows a more useful PTT sensing process. For example, an oscillometric cuff is not required. A benefit of PTT is that it can be used to more continually monitor blood pressure compared to many other techniques including possibly those of embodiments 1 and 2.

In certain embodiments, the biometric monitoring device contains blood pressure sensor as described herein, as well as a PTT measurement sensor. PTT may be measured via an EKG and PPG (e.g., where the device has electrodes that the user holds for EKG) or BCG and PPG (e.g., BCG from accelerometer in the device and captured while the user is stationary). The user of the device may perform a blood pressure measurement with the aforementioned blood pressure sensor, and these measurements may be used to calibrate a relationship between PTT and blood pressure, from which the PTT system may provide (in the BCG embodiment) more continuous measurements of the user's blood pressure.

In certain embodiments, the one or more processors of the biometric monitoring device are configured to: (i) obtain pulse transit time (PTT) data for the user; and (ii) calibrate the PTT data using the user's blood pressure determined from the variation of PPG blood volume pulse amplitude with variation in applied pressure to the location where the PPG presses against the user's body. In some implementations, the one or more processors are configured to: (i) obtain the PTT data at first rate, and (ii) determine the user's blood pressure from the variation of PPG blood volume pulse amplitude with variation in applied pressure at a second rate. The first rate may be greater than the second rate.

In certain embodiments, a biometric monitoring device of any type described herein for estimating user blood pressure additionally includes an EKG electrode configured to be placed on a portion of the user's body where the EKG electrode generates EKG electrode data for determining PTT.

In certain embodiments, the one or more processors are configured to obtain the PTT data from (i) the PPG sensor data, which is used for obtaining blood volume amplitude data the processor(s) use with force or pressure data described herein, and (ii) data from another sensor. As examples, the other sensor may be an EKG electrode, a phonocardiography (PCG) sensor, ballistocardiography (BCG) sensor, an impedance plethysmography (IPG) sensor, a ultrasound sensor, and a force sensor. In certain embodiments, the one or more processors are further configured to generate the PTT data by using the EKG electrode data and the PPG sensor data.

Additional description of devices and methods to facilitate generating and interpreting PTT data are provided in U.S. patent application Ser. No. 15/414,425 filed Jan. 24, 2017 and in U.S. Provisional Patent Application No. 62/286,876 filed Jan. 25, 2016, both naming Pantelopoulos et al. as inventors and both incorporated herein by reference in their entireties. Wrist Worn Devices and Other Wearable Fixing Structures As explained, the wearable fixing structure may be designed to fix to the user or the user's apparel in many ways. It may also include features for physically attaching to, encasing, or enclosing the one or more processors, the blood pulse amplitude sensor, and/or the force or pressure sensor. In one example, a PPG sensor, the force or pressure sensor (e.g., a force sensitive touch screen), and the one or more processors are integrated in the wearable fixing structure. Further, the force sensor and the PPG sensor may be within and/or directly attached to an enclosure that is part of or affixed to the wearable fixing structure. In certain embodiments, the device includes a protrusion from the wearable fixing structure, wherein the PPG sensor and the force or pressure sensor are disposed within the protrusion.

In certain embodiments, the biometric monitoring device additionally includes a wireless transmitter configured to transmit blood pulse amplitude data (e.g., PPG sensor data) and variable force and/or pressure data to a remote device. The transmitter may be attached to or contained in the wearable fixing structure. In certain embodiments, the one or more processors are located in the remote device. The remote device may be, for example, a smart phone, a tablet, a personal computer (e.g., a laptop computer), a server, a distributed computing environment, and the like.

While the term wrist "band" is used herein, it is intended to cover all types of structure for fixing the sensor(s) to the user's wrist. The band may have a wide range of rigidities, so long as it can conform generally to the shape of the user's wrist. The concept of a wrist band includes flexible wrist straps and bracelets with links. It also includes fixing structures that attach to watch faces and the like.

Biometric monitoring devices and associated sensors, including PPG sensors, processing logic, and the like are described in more detail in U.S. patent application Ser. No. 15/414,425 filed Jan. 24, 2017 and in U.S. Provisional Patent Application No. 62/286,876 filed Jan. 25, 2016, both naming Pantelopoulos et al. as inventors and both incorporated herein by reference in their entireties.

OTHER EMBODIMENTS

It is to be understood that biometric monitoring devices, in addition to including the features recited below, may also include one or more features or functionalities discussed above or discussed in the applications incorporated by reference in the above discussion. Such implementations are to be understood as being within the scope of this disclosure.

There are many concepts and embodiments described and illustrated herein. While certain embodiments, features, attributes, and advantages have been described and illustrated herein, it should be understood that many others, as well as different and/or similar embodiments, features, attributes and advantages are apparent from the description and illustrations. As such, the above embodiments are merely provided by way of example. They are not intended to be exhaustive or to limit this disclosure to the precise forms, techniques, materials and/or configurations disclosed. Many modifications and variations are possible in light of this disclosure. It is to be understood that other embodiments may be utilized and operational changes may be made without departing from the scope of the present disclosure. As such, the scope of the disclosure is not limited solely to the description above because the descriptions of the above embodiments have been presented for the purposes of illustration and description.

The present disclosure is neither limited to any single aspect nor embodiment, nor to any combinations and/or permutations of such aspects and/or embodiments. Moreover, each of the aspects of the present disclosure, and/or embodiments thereof, may be employed alone or in combination with one or more of the other aspects and/or embodiments thereof. For the sake of brevity, many of those permutations and combinations will not be discussed and/or illustrated separately herein.

The invention claimed is:

1. A wearable device wearable on an appendage of a user, comprising:
a force-sensitive display screen configured to generate force data when a force is applied to the force-sensitive display screen;
a photoplethysmogram (PPG) sensor, positioned below an external surface of the force-sensitive display screen, the PPG sensor being configured to generate PPG sensor data when the force is applied to the force-sensitive display screen, the PPG sensor data representing blood volume pulses of variable amplitude at the appendage caused by the force being applied to the force-sensitive display screen; and
one or more processors configured to:
determine, from the PPG sensor data and the force data, a variation of PPG blood volume pulse amplitude with a variation in pressure applied to the appendage, and
calculate an estimate of blood pressure of the appendage from the variation of PPG blood volume pulse amplitude with the variation in the pressure applied to the appendage, by determining a diastolic pressure and a systolic pressure, the diastolic pressure being determined based on a first ratio of a first PPG blood volume pulse amplitude from the PPG sensor data to a peak PPG blood volume pulse amplitude from the PPG sensor data, and the systolic pressure being determined based on a second ratio of a second PPG blood volume pulse amplitude from the PPG sensor data to the peak PPG blood volume pulse amplitude.

2. The wearable device of claim 1, wherein the PPG sensor is housed in a body disposed below the force-sensitive display screen, the body being in direct contact with the appendage when the wearable device is worn on the appendage of the user.

3. The wearable device of claim 1, wherein the one or more processors are configured to generate one or more sensor data samples, each of the one or more sensor data samples comprising data that links the force data generated when the force is applied to the force-sensitive display screen at a given time with the PPG sensor data obtained from at least one light detector of the PPG sensor at the given time.

4. The wearable device of claim 1, wherein the force-sensitive display screen comprises a piezo resistive force-sensitive display screen.

5. The wearable device of claim 1, wherein the appendage comprises a wrist, an ankle, a finger, a toe, a torso, a neck, an upper arm, or a waist.

6. The wearable device of claim 1, wherein the PPG sensor includes at least one light emitter configured to emit light outside a visible portion of the electromagnetic spectrum.

7. The wearable device of claim 6, wherein the at least one light emitter is an infrared light emitter.

8. The wearable device of claim 1, wherein the one or more processors are configured to control the force-sensitive display screen to depict a marking of an area of the force-sensitive display screen to which the force is to be applied.

9. The wearable device of claim 1, wherein
the force-sensitive display screen comprises a greater density of pixels in a central portion of the force-sensitive display screen than in a peripheral portion of the force-sensitive display screen, and the central portion of the force-sensitive display screen is a location where the force is to be applied to the force-sensitive display screen to cause the force data to be generated.

10. The wearable device of claim 1, wherein the one or more processors are configured to use the force data and an area of an object applying the force to the force-sensitive display screen to derive pressure applied by the object applying the force to the force-sensitive display screen.

11. The wearable device of claim 1, wherein the blood volume pulses of variable amplitude are generated by at least one of a capillary bed proximate to the appendage or an artery proximate to the appendage.

12. The wearable device of claim 1, wherein the one or more processors and/or the force-sensitive display screen are configured to determine pressure produced when the force is applied to the force-sensitive display screen.

13. The wearable device of claim 1, wherein the one or more processors and/or the force-sensitive display screen are configured to:

determine an area occupied by pixels of the force-sensitive display screen which detect the force applied to the force-sensitive display screen and cause the PPG sensor to generate the PPG sensor data; and determine pressure by using the force data from the force-sensitive display screen together with the area occupied by the pixels of the force-sensitive display screen.

14. The wearable device of claim 1, wherein the one or more processors and/or the force-sensitive display screen are configured to dynamically oversample an area of the force-sensitive display screen detected to be in contact with an object applying the force to the force-sensitive display screen.

15. The wearable device of claim 1, wherein the one or more processors and/or the force-sensitive display screen are configured to determine pressure produced when the force is applied to the force-sensitive display screen and causes the PPG sensor to generate the PPG sensor data, and the one or more processors and/or the force-sensitive display screen are configured to determine the pressure using the force data, and an area of a capture structure disposed on the wearable device against which the force is applied to the force-sensitive display screen.

16. The wearable device of claim 1, wherein the one or more processors are further configured to control the force-sensitive display screen to present instructions to apply a force to a location on the wearable device.

17. The wearable device of claim 1, wherein
the one or more processors are configured to convert the force data to pressure values based on a variable area of an object applying the force to the force-sensitive display screen, to determine the variation in pressure applied to the appendage, and
the one or more processors and/or the force-sensitive display screen are configured to dynamically determine the variable area of the object applying the force to the force-sensitive display screen by determining an area of pixels which occupy a part of the force-sensitive display screen and which detect a force caused when the object applies the force to the force-sensitive display screen.

18. The wearable device of claim 1, wherein
the first ratio is greater than the second ratio.

19. A biometric device, comprising:
a force sensor configured to generate force data when a force is applied to the force sensor;
a photoplethysmogram (PPG) sensor, positioned below an external surface of the force sensor, the PPG sensor being configured to generate PPG sensor data when the force is applied to the force sensor, the PPG sensor data representing blood volume pulses of variable amplitude at a body part of a user caused by the force being applied to the force sensor when the biometric device is worn by the user; and
one or more processors configured to:
determine, from the PPG sensor data and the force data, a variation of PPG blood volume pulse amplitude with a variation in pressure applied to the body part, and
calculate an estimate of blood pressure of the body part from the variation of PPG blood volume pulse amplitude with the variation in the pressure applied to the body part, by determining a diastolic pressure and a systolic pressure, the diastolic pressure being determined based on a first ratio of a first PPG blood volume pulse amplitude from the PPG sensor data to a peak PPG blood volume pulse amplitude from the PPG sensor data, and the systolic pressure being determined based on a second ratio of a second PPG blood volume pulse amplitude from the PPG sensor data to the peak PPG blood volume pulse amplitude.

20. The biometric device of claim 19, wherein
the first ratio is greater than the second ratio.

* * * * *